US007115730B1

(12) United States Patent
Pizza et al.

(10) Patent No.: US 7,115,730 B1
(45) Date of Patent: Oct. 3, 2006

(54) **IMMUNOGENIC DETOXIFIED MUTANT *E. COLI* LT-A-TOXIN**

(75) Inventors: Mariagrazia Pizza, Siena (IT); Marzia Monica Giuliani, Siena (IT); Rino Rappuoli, Caste Inuovo Berardenga (IT)

(73) Assignee: Chiron SRL, Siena (IT)

( * ) Notice: Subject to any disclaimer, the term of this patent is extended or adjusted under 35 U.S.C. 154(b) by 0 days.

(21) Appl. No.: 09/528,682

(22) Filed: Mar. 20, 2000

Related U.S. Application Data

(62) Division of application No. 09/297,171, filed on Apr. 27, 1999, now abandoned.

(51) Int. Cl.
*C07H 21/02* (2006.01)
*A01N 21/04* (2006.01)

(52) U.S. Cl. ............... 536/23.7; 536/23.1; 424/278.1; 435/69.1; 935/60

(58) Field of Classification Search ............ 424/278.1; 435/69.1; 935/60; 536/23.7
See application file for complete search history.

(56) References Cited

U.S. PATENT DOCUMENTS

| 5,182,109 A | 1/1993 | Tamura et al. | |
| 5,770,203 A * | 6/1998 | Burnette et al. | 424/190.1 |

FOREIGN PATENT DOCUMENTS

| EP | 0 145 486 | 12/1984 |
| EP | 145486 | * 6/1985 |
| EP | 0396964 | 11/1990 |
| EP | 0462534 | 12/1991 |
| WO | WO 92/19265 | 11/1992 |
| WO | WO 92/22326 | 12/1992 |
| WO | 93/13202 | * 7/1993 |
| WO | WO 93/13202 | 7/1993 |
| WO | WO 95/09649 | 4/1995 |
| WO | WO 95/17211 | 6/1995 |
| WO | WO 95/34323 | 12/1995 |
| WO | WO 96/06627 | 3/1996 |
| WO | WO 97/02348 | 1/1997 |
| WO | WO 99/58145 | 11/1999 |
| WO | WO 00/18434 | 4/2000 |

OTHER PUBLICATIONS

Bowen et al., "Cholera Toxin Acts as a Potent Adjuvant for Induction of Cytotoxic T-Lymphocyte Responses with Non-Replicating Antigents," *Immunology* 81:338-342 (1994).
Burnette et al., "Site-Specific Mutagenesis of the Catalytic Subunit of Cholera Toxin: Substituting Lysine for Arginine 7 Causes Loss of Activity," *Inf. & Immunity* 59(11):4266-4270 (1991).
Clements et al., "Adjuvant Activity of *Escherichia coli* Heat-Labile Enterotoxin and Effect on the Induction of Oral Tolerance in Mice to Unrelated Protein Antigens," *Vaccine* 6:269-277 (1988).

(Continued)

Primary Examiner—Michael Borin
(74) Attorney, Agent, or Firm—Rebecca M. Hale; Dahna S. Pasternak; Alisa A. Harbin

(57) ABSTRACT

An immunogenic detoxified protein is provided which comprises the amino acid sequence of subunit A of an *E. coli* heat labile toxin (LT-A) or a fragment thereof in which at least amino acid Ala-72, numbered relative to SEQ ID NO:1, of the A subunits mutated, preferably by substitution with Arg. The toxoid is useful as vaccine against an enterotoxigenic strain of *E. coli* and is produced by recombinant DNA means by site-directed mutagenesis. It is also an effective adjuvant.

26 Claims, 13 Drawing Sheets

```
           1                                                        50
SEQ ID NO 1  NGDRLYRADS RPPDEIKRSG GLMPRGHNEY FDRQTQMNIN LYDHARGTQT
SEQ ID NO 2  ---K------ ---------- ---------- ---------- ----------
SEQ ID NO 3  -D..FF---- -T----R-A- --L---QQ-A YE---PI--- --E-----V-
SEQ ID NO 4  -D..YF---- -T---VR--- --I---QD-A YE---PI--- --------A-

51                                                      100
SEQ ID NO 1  GFVRYDDGYV STSLSLRSAH LAGQSILSGY STYYIYVIAT APNMFNVNDV
SEQ ID NO 2  ---------- ---------- ---------- ---------- ----------
SEQ ID NO 3  -NT--N---- --TVF--Q-- -I--N--GS- NE-----V-P ---L-D--G-
SEQ ID NO 4  -NT--N---- --TTT--Q-- FL--NM-G-- NE-----V-A --L-D--G-

101                                                     150
SEQ ID NO 1  LGVYSPHPYE QEVSALGGIP YSQIYGWYRV NFGVIDERLH RNREYRDRYY
SEQ ID NO 2  ---------- ---------- ---------- ---------- ----------
SEQ ID NO 3  --R---Y-S- N-FA------ L---I----- S--A-EGGMQ ---D--GDLF
SEQ ID NO 4  --R---Y-S- N-YA------ L---I----- S--A-EGGM- ---D--RDLF 151                                                     200
SEQ ID NO 1  RNLNIAPAED GYRLAGFPPD HQAWREEPWI HHAPQGCGNS SRTITGDTCN
SEQ ID NO 2  ---------- ---------- ---------- ---------- ----------
SEQ ID NO 3  -G-TV--N-- --Q-----SN FP----M--S TF--EQ-VPN NKEFK-GV-I
SEQ ID NO 4  -G-SA--N-- ---I----DG FP--E-V--R EF--N5-LPN NKASSDT--A 201                                240
SEQ ID NO 1  EETQNLSTIY LREYQSKVKR QIFSDYQSEV DIYNRIRDEL
SEQ ID NO 2  ---------- ---K------ ---------- -------N--
SEQ ID NO 3  SA-NV--KYD -MNFXKLL-- RFM-..EDDF IGVHG8----
SEQ ID NO 4  SL-NK--QHD -ADFKKYI-- KLL-INNDGF PSNNGGK---
                                     |
                                  LALTF
                                  FC-MT
```

OTHER PUBLICATIONS

Di Tommaso et al., "Induction of Antigen-Specific Antibodies in Vaginal Secretions by Using a Nontoxic Mutant of Heat-Labile Enterotoxin as a Mucosal Adjuvant," *Inf. & Immunity* 64(3):974-979 (1996).

Domenighini et al., "MicroCorrespondence," *Mol. Microbiology* 15(6):1165-1167 (1995).

Douce et al., "Mutants of *Escherichia coli* Heat-Labile Toxin Lacking ADP- Ribosyltransferase Activity Act as Nontoxic, Mucosal Adjuvants," *Proc. Natl. Acad. Sci.* 92:1644-1648 (1995).

Douce et al., "Intranasal Immunogenicity and Adjuvanticity of Site-Directed Mutant Derivatives of Cholera Toxin," *Inf. & Immunity* 65(7):2821-2828 (1997).

Fontana et al., "Construction of Nontoxic Derivatives of Cholera Toxin and Characterization of Immunological Response Against the A Subunit," *Inf. & Immunity* 63(6):2356-2360 (1995).

Harford et al., "Inactivation of the *Escherichia coli* Heat-Labile Enterotoxin by Invitro Mutagenesis," *Eur. J. Biochem* 183:311-316 (1989).

Holmgren et al., "An Oral B Subunit: Whole Cell Vaccine Against Cholera," *Vaccine* 10(3):911-914 (1992).

Holmgren et al., "Cholera Toxin and Cholera B Subunit as Oral-Mucosal Adjuvant and Antigen Vector Syst ms," *Vaccine* 11(13):1179-1183 (1993).

Jackson et al., "Optimizing Oral Vaccines: Induction of Systemic and Mucosal B-Cell and Antibody Responses to Tetanus Toxoid by Use of Cholera Toxin as an Adjuvant," *Inf & Immunity* 61(10):4272-4279 (1993).

Lycke et al., "The Adjuvant Effect of Vibrio Cholera and *Escherichia coli* Heat-Labile Enterotoxins is Linked to their ADP-Ribosyltransferase," *Eur. J. Immunol.* 22:2277-2281 (1992).

Magagnoli et al., "Mutations in the A Subunit Affect Yield, Stability, and Potease Sensitivity og Nontoxic Derivatives of Heat-Labile Enterotoxin," *Inf & Immunity* 64(12):5434-5438 (1996).

Nashar et al., "Potent Immunogenicity of the B Subunits of *Escherichia coli* Heat-Labile Enterotoxin: Receptor Binding is Essential and Induces Differential Modulation of Lumphocyte Subsets," *Proc. Natl. Acad. Sci.* 93:226-230 (1996).

Partidos et al., "The Adjuvant Effect of a Non-Toxic Mutant of Heat-Labile Enterotoxin of *Escherichia coli* for the Induction of Measles Virus-Specific CTL Responses After Intranasal Co-Immunization with a Synthetic Peptide," *Immunology* 89:483-487 (1996).

Pizza et al., "Probing the Structure-Activity Relationship of *Escherichia coli* LT-A by Site-Directed Mutagenesis," *Moloecular Microbiology* 14(1):51-60 (1994).

Rollwagen et al., "Killed Campylobacter Elicits Immune Response and Protection When Administered With an Oral Adjuvant," *Vaccine* 11(13):1316-1320 (1993).

Snider, Dennis P., "The Mucosal Adjuvant Activities of ADP-Ribosylating Bacterial Enterotoxins," *Critical Reviews in Immunology* 15(3&4):317-348 (1995).

Tsuji et al., "A Single Amino Acid Substitution in the A Subunit of *Escherichia coli* Enterotoxin Results in a Loss of its Toxic Activity," *Journal of Biological Chemistry* 265(36):22520-22525 (1990).

van den Akker et al., "The Arg7Lys Mutant of Heat-Labile Enterotoxin Exhibits Great Flexibility of Active Site Loop 47-56 of the Subunit,"*Biochemistry* 34 :10996-11004 (1995).

Wilson et al., "Adjuvant Action of Cholera Toxin and Pertussis Toxin in the Induction of IgA Antibody Response to Orally Administered Antigen," *Vaccine* 11(2):113-118 (1993).

Burnette, "The Advent of Recombinant Pertussis Vaccines." *Biotechnol.* 8:1002-1005 (1990).

Burnette, *Vaccine Research & Developments* Chapter 6, Marcel Dekker Inc., New York, New York (1992).

Communication to EPO Concerning Replacement Claims for Filing with the EPO in Application No. 99922284.7 (2003).

de Haan, et al., "Mutational Analysis of the Role of ADP-Ribosylation Activity in the Adjuvant Properties of the *Escherichia coli* Heat-Labile Enterotoxin Towards Intranasally Administered Keyhole Limpet Hemocyanin." *Eur. J. Immunol.* 28:1243-1250 (1998).

Del Guidice, et al., "Genetically Derived Toxoids for use as Vaccines and Adjuvants." *Vaccine* 17:S44-S52 (1999).

Dickinson & Clements, "Dissociation of *Escherichia coli* heat-labile enterotoxin adjuvanticity from ADP-ribosyltransferase activity", Infect. Immunity, 63:1617-1623 (1995).

EPO Communication pursuant to Article 96(2) EPC relating to Application EP No. 94928455.8-2116 (2001).

"Multicomponent Vaccine Development." *NIH Guide* vol. 22, No. 28 (1993).

Green, Bruce, Curriculum Vitae.

Grant et al., "Role of trypsin-like cleavage at arginine 192 in the enzymatic and cytotonic activities of *Escherichia coli* heat-labile enterotoxin", Infect. Immun., 62:4270-4278 (1994).

Hagen, Michael, Cirriculum Vitae.

Hagiwar, et al., Effectiveness and Safety of Mutant *Escherichia coli* Heat-Labile Enterotoxin (LT H44A) as an Adjuvant for Nasal Influenza Vaccine. *Vaccine* 19:2071-2079 (2001).

Hartman, et al., "Native and Mutant Forms of Cholera Toxin and Heat-Labile Enterotoxin Effectively Enhance Protective Efficacy of Live Attenuated and Heat-Killed Shigella Vaccines." *Infect. Immun.* 67:5841-5847 (1999).

Hazama, et al., "Intranasal Immunization Against Herpes Simplex Virus Infection by using a Recombinant Glycoprotein D Fused with Immunomodulating Proteins, the B Subunit of *Escherichia coli* Heat-Labile Enterotoxin and Interleukin-2." *Immunology* 78:643-649 (1993).

Hirst, et al., "Cholera Toxin and Related Enterotoxins as Potent Immune Modulators." *J. Appl. Microb. Symp. Suppl.* 48:26S-34S (1998).

Hirst, *The Comprehensive Sourcebook of Bacterial Protein Toxins*, Chapter 6, Academic Press, pp. 104-130, (1999).

Lobet et al.., "Effect of site-directed mutagenic alterations on ADP-ribosyltransferase activity of the A subunit of *Escherichia coli* heat-labile enterotoxin", Infect. Immun. 59:2870-2879 (1991).

Lycke, et al., "Strong Adjuvant Properties of Cholera Toxin on Gut Mucosal Immune Responses to Orally Presented Antigens." *Immunol.* 56:301-308 (1986).

Lycke, et al, "the Mechanism of Cholera Toxin Adjuvanticity." *Res. Immunol.* 198 :504-520 (1997).

Martindale, *Royal Pharmaceutical Society of Britain* Pharmaceutical Press, London, England, pp. 1277-1304(1993).

Rappouli, et al., "Structure and Mucosal Adjuventicity of Cholera and *Escherichia coli* Heat-Labile Enterotoxins." *Immunol. Today* 20:493-500 (1999).

Spangler, "Structure and Function of Cholera Toxin and The Related *Escherichia coli* Heat-Labile Enterotoxin." *Microbiol. Rev.* 56:622-647 (1992).

Streatfield, et al. , "Intermolecular Interactions Between the A and B Subunits of Heat-Labile Enterotoxin from *Escherichia coli* Promote Holotoxin Assembly and Stability In Vivo." *PNAS USA* 89:12140-12144 (1992).

*The Comprehensive Sourcebook of Bacterial Protein Toxins*, $2^{nd}$ Ed., Academic Press, pp. 696-697.

Tsuji, et al., "Relationship Between a Low Toxicity of the Mutant A Subunit of Entertoxigenic *Escherichia coli* Enterotoxin and its Strong Adjuvant Action." *Immunology* 90:176-182 (1997).

Verweij, et al.,Mucosal Immunoadjuvant Activity of Recombinant *Escherichia coli* Heat-Labile Enterotoxin and its B Subunit: Induction of Systematic IgG and Secretory IgA Responses in Mice by Intranasal Immunization with Influenza Virus Surface Antigen. *Vaccine* 16:2069-2076 (1998).

Walker, et al., "Use of Heat-Labile Toxin Enterotoxigenic *Escherichia coli* to Facilitate Mucosal Immunization." *Vaccine Res.* 2:1-10 (1993).

Williams, Neil, Affidavit, Curriculum Vitae, and Annex 1.

Yamamoto, et al., "Mutants in the ADP-Ribosyltransferase Cleft of Cholera Toxin Lack Diarrheagenicity but Retain Adjuvanticity." *J. Exp. Med.* 185:1203-1210 (1997).

\* cited by examiner

```
            1                                                        50
SEQ ID NO 1 NGDRLYRADS RPPDEIKRSG GLMPRGHNEY FDRQTQMNIN LYDHARGTQT
SEQ ID NO 2 ---K------ ---------- ---------- ---------- ----------
SEQ ID NO 3 -D..FF---- -T----R-A- --L---QQ-A YE---PI--- --E------V-
SEQ ID NO 4 -D..YF---- -T---VR--- --I---QD-A YE---PI--- --------A-

51                                                       100
SEQ ID NO 1 GFVRYDDGYV STSLSLRSAH LAGQSILSGY STYYIYVIAT APNMFNVNDV
SEQ ID NO 2 ---------- ---------- ---------- ---------- ----------
SEQ ID NO 3 -NT--N---- --TVT--Q-- -I--N--GS- NE-----V-P ---L-D--G-
SEQ ID NO 4 -NT--N---- --TTT--Q-- FL--NM-G-- NE-----V-A ---L-D--G-

101                                                      150
SEQ ID NO 1 LGVYSPHPYE QEVSALGGIP YSQIYGWYRV NFGVIDERLH RNREYRDRYY
SEQ ID NO 2 ---------- ---------- ---------- ---------- ----------
SEQ ID NO 3 --R---Y-S- N-FA------ L---I----- S--A-EGGMQ ---D--GDLF
SEQ ID NO 4 --R---Y-S- N-YA------ L---I----- S--A-EGGM- ---D--RDLF 151                                                      200
SEQ ID NO 1 RNLNIAPAED GYRLAGFPPD HQAWREEPWI HHAPQGCGNS SRTITGDTCN
SEQ ID NO 2 ---------- ---------- ---------- ---------- ----------
SEQ ID NO 3 -G-TV--N-- --Q-----SN FP-----M--S TF--EQ-VPN NKEFK-GV-I
SEQ ID NO 4 -G-SA--N-- ---I----DG FP--E-V--R EF--NS-LPN NKASSDT--A 201                            240
SEQ ID NO 1 EETQNLSTIY LREYQSKVKR QIFSDYQSEV DIYNRIRDEL
SEQ ID NO 2 ---------- --K------- ---------- -------N--
SEQ ID NO 3 SA-NV--KYD -MNFKKLL-- RFM-..EDDF IGVHGE----
SEQ ID NO 4 SL-NK--QHD -ADFKKYI-- KLL-INNDGF FSNNGGK---
                                   LALTF
                                   FT-MT
```

FIG. 12

SEQUENCE LISTING

<160> NUMBER OF SEQ ID NOS: 5

<210> SEQ ID NO 1
<211> LENGTH: 240
<212> TYPE: PRT
<213> ORGANISM: Escherichia coli

<400> SEQUENCE: 1

```
Asn Gly Asp Arg Leu Tyr Arg Ala Asp Ser Arg Pro Pro Asp Glu Ile
 1               5                  10                  15

Lys Arg Ser Gly Gly Leu Met Pro Arg Gly His Asn Glu Tyr Phe Asp
            20                  25                  30

Arg Gly Thr Gln Met Asn Ile Asn Leu Tyr Asp His Ala Arg Gly Thr
        35                  40                  45

Gln Thr Gly Phe Val Arg Tyr Asp Asp Gly Tyr Val Ser Thr Ser Leu
    50                  55                  60

Ser Leu Arg Ser Ala His Leu Ala Gly Gln Ser Ile Leu Ser Gly Tyr
65                  70                  75                  80

Ser Thr Tyr Tyr Ile Tyr Val Ile Ala Thr Ala Pro Asn Met Phe Asn
                85                  90                  95

Val Asn Asp Val Leu Gly Val Tyr Ser Pro His Pro Tyr Glu Gln Glu
            100                 105                 110

Val Ser Ala Leu Gly Gly Ile Pro Tyr Ser Gln Ile Tyr Gly Trp Tyr
        115                 120                 125

Arg Val Asn Phe Gly Val Ile Asp Glu Arg Leu His Arg Asn Arg Glu
    130                 135                 140

Tyr Arg Asp Arg Tyr Tyr Arg Asn Leu Asn Ile Ala Pro Ala Glu Asp
145                 150                 155                 160

Gly Tyr Arg Leu Ala Gly Phe Pro Pro Asp His Gln Ala Trp Arg Glu
                165                 170                 175

Glu Pro Trp Ile His His Ala Pro Gln Gly Cys Gly Asn Ser Ser Arg
            180                 185                 190

Thr Ile Thr Gly Asp Thr Cys Asn Glu Glu Thr Gln Asn Leu Ser Thr
        195                 200                 205

Ile Tyr Leu Arg Glu Tyr Gln Ser Lys Val Lys Arg Gln Ile Phe Ser
    210                 215                 220

Asp Tyr Gln Ser Glu Val Asp Ile Tyr Asn Arg Ile Arg Asp Glu Leu
225                 230                 235                 240
```

<210> SEQ ID NO 2
<211> LENGTH: 3
<212> TYPE: PRT
<213> ORGANISM: Escherichia coli

<400> SEQUENCE: 2

```
Lys Lys Asn
 1
```

<210> SEQ ID NO 3
<211> LENGTH: 107
<212> TYPE: PRT
<213> ORGANISM: Escherichia coli

<400> SEQUENCE: 3

```
Asp Phe Phe Thr Arg Ala Leu Gln Gln Ala Tyr Glu Pro Ile Glu Val
 1               5                  10                  15
```

```
Asn Thr Asn Thr Val Thr Gln Ile Asn Gly Ser Asn Glu Val Pro Leu
            20                  25                  30

Asp Gly Arg Tyr Ser Asn Phe Ala Leu Ile Ser Ala Glu Gly Gly Met
        35                  40                  45

Gln Asp Gly Asp Leu Phe Gly Thr Val Asn Gln Ser Asn Phe Pro Met
    50                  55                  60

Ser Thr Phe Glu Gln Val Pro Asn Asn Lys Glu Phe Lys Gly Val Ile
65                  70                  75                  80

Ser Ala Asn Val Lys Tyr Asp Met Asn Phe Lys Lys Leu Leu Arg Phe
                85                  90                  95

Met Glu Asp Asp Phe Ile Gly Val His Gly Glu
            100                 105
```

<210> SEQ ID NO 4
<211> LENGTH: 110
<212> TYPE: PRT
<213> ORGANISM: Escherichia coli

<400> SEQUENCE: 4

```
Asp Tyr Phe Thr Val Arg Ile Gln Asp Ala Tyr Glu Pro Ile Ala Asn
1               5                   10                  15

Thr Asn Thr Thr Thr Gln Phe Leu Asn Met Gly Asn Glu Val Ala Leu
            20                  25                  30

Asp Gly Arg Tyr Ser Asn Tyr Ala Leu Ile Ser Ala Glu Gly Gly Met
        35                  40                  45

Asp Arg Asp Leu Phe Gly Ser Ala Asn Ile Asp Gly Phe Pro Glu Val
    50                  55                  60

Arg Glu Phe Asn Ser Leu Pro Asn Asn Lys Ala Ser Ser Asp Thr Ala
65                  70                  75                  80

Ser Leu Asn Lys Gln His Asp Ala Asp Phe Lys Lys Tyr Ile Lys Leu
                85                  90                  95

Leu Ile Asn Asn Asp Gly Phe Phe Ser Asn Asn Gly Gly Lys
            100                 105                 110
```

<210> SEQ ID NO 5
<211> LENGTH: 240
<212> TYPE: PRT
<213> ORGANISM: Escherichia coli

<400> SEQUENCE: 5

```
Asn Gly Asp Arg Leu Tyr Arg Ala Asp Ser Arg Pro Pro Asp Glu Ile
1               5                   10                  15

Lys Arg Ser Gly Gly Leu Met Pro Arg Gly His Asn Glu Tyr Phe Asp
            20                  25                  30

Arg Gly Thr Gln Met Asn Ile Asn Leu Tyr Asp His Ala Arg Gly Thr
        35                  40                  45

Gln Thr Gly Phe Val Arg Tyr Asp Asp Gly Tyr Val Ser Thr Ser Leu
    50                  55                  60

Ser Leu Arg Ser Ala His Leu Ala Gly Gln Ser Ile Leu Ser Gly Tyr
65                  70                  75                  80

Ser Thr Tyr Tyr Ile Tyr Val Ile Ala Thr Ala Pro Asn Met Phe Asn
                85                  90                  95

Val Asn Asp Val Leu Gly Val Tyr Ser Pro His Pro Tyr Glu Gln Lys
            100                 105                 110

Val Ser Ala Leu Gly Gly Ile Pro Tyr Ser Gln Ile Tyr Gly Trp Tyr
        115                 120                 125
```

-continued

| | | | | | | | | | | | | |
|---|---|---|---|---|---|---|---|---|---|---|---|---|
| Arg | Val | Asn | Phe | Gly | Val | Ile | Asp | Glu | Arg | Leu | His | Gly | Asn | Arg | Glu |
| | | 130 | | | | 135 | | | | 140 | | |
| Tyr | Arg | Asp | Arg | Tyr | Tyr | Arg | Asn | Leu | Asn | Ile | Ala | Pro | Ala | Glu | Asp |
| 145 | | | | | 150 | | | | | 155 | | | | | 160 |
| Gly | Tyr | Arg | Leu | Ala | Gly | Phe | Pro | Pro | Asp | His | Gln | Ala | Trp | Arg | Glu |
| | | | | 165 | | | | | 170 | | | | | 175 | |
| Glu | Pro | Trp | Ile | His | His | Ala | Pro | Gln | Gly | Cys | Gly | Asn | Ser | Ser | Arg |
| | | | | 180 | | | | | 185 | | | | | 190 | |
| Thr | Ile | Thr | Gly | Asp | Thr | Cys | Asn | Glu | Glu | Thr | Gln | Asn | Leu | Ser | Thr |
| | | | 195 | | | | | 200 | | | | | 205 | | |
| Ile | Tyr | Leu | Arg | Glu | Tyr | Gln | Ser | Lys | Val | Lys | Arg | Gln | Ile | Phe | Ser |
| | | | 210 | | | | 215 | | | | | 220 | | | |
| Asp | Tyr | Gln | Ser | Glu | Val | Asp | Ile | Tyr | Asn | Arg | Ile | Arg | Asp | Glu | Leu |
| 225 | | | | | 230 | | | | | 235 | | | | | 240 |

IMMUNOGENIC DETOXIFIED MUTANT E. COLI LT-A-TOXIN

CROSS-REFERENCE TO RELATED APPLICATION

This application is a divisional of U.S. patent application Ser. No. 09/297,171, filed Apr. 27, 1999, now abandoned from which priority is claimed under 35 USC § 120 and which is incorporated herein by reference in its entirety.

FIELD OF THE INVENTION

The present invention relates to immunogenic detoxified heat labile toxin proteins (LT) produced by enterotoxigenic strains of Escherichia coli (E. coli) wherein at least amino acid Ala-72 of the A subunit is mutated, and to their use in vaccines which are useful in the prevention or treatment of enterotoxigenic E. coli infections and as adjuvants for other immunogenic proteins. Toxoids of the invention can be suitably produced using recombinant DNA techniques by site-directed mutagenesis of DNA encoding the wild-type toxins.

BACKGROUND TO THE INVENTION

Heat-labile enterotoxin (LT), produced by enterotoxigenic strains of E. coli, and cholera toxin (CT), produced by V. cholerae strains, are the causative agents of traveller's diarrhoea and cholera, respectively [Spangler (1992) Microbiol Rev 56:622]. LT and CT show 80% homology in the primary structure and an identical tertiary structure. They are composed of two functionally distinct domains: the enzymatically-active A subunit and the B pentamer, which contains the receptor-binding site. The A subunit ADP-ribosylates the target protein Gs, a GTP-binding protein which regulates the intracellular levels of cAMP [Rappuoli & Pizza (1991), in Sourcebook of bacterial protein toxins, Academic Press NY]. Enhancement in cAMP levels can alter ion transport, inducing secretion of water and chloride ions into the intestine.

CT and LT are both powerful immunogens and potent mucosal adjuvants when co-administered with antigens at the mucosal level [eg. Jackson et al. (1993) Infect Immun 61:4272; WO95/17211]. Immunogenicity and adjuvanticity of wild-type CT and LT have been extensively studied in animals [eg. Rollwagen et al. (1993) Vaccine 11:1316], but their toxicity has precluded their use in humans. In an attempt to overcome the problems generated by the use of active holotoxins, two different approaches have been followed, one based on the use of the B pentamer, the non-toxic domain of the holotoxin [eg. Holmgren et al. (1992) Vaccine 10:911], and the other based on the generation of genetically detoxified derivatives of LT and CT [eg. Fontana et al. (1995) Infect Immun 63:2356]. Site-directed mutagenesis on both A and B subunits has provided a tool to explore the basis of the immunological and adjuvant responses induced by these molecules.

Examples of such experiments can be found in:

Harford et al. [Eur J Biochem (1989) 183:311] made LT-A carrying Ser-61-Phe and Gly-79-Lys substitutions.

Tsuji et al. [J Biol Chem (1990) 265:22520] produced LT-A carrying a Glu-112-Lys substitution.

Burnette et al. [Infect Immun (1991) 59:4266] produced CT-A carrying a Arg-7-Lys substitution. This work can also be seen in WO92/19265.

WO93/13202 described non-toxic CT and LT carrying mutations at Val-53, Ser-63, Val-97, Tyr-104, and Pro-106

A mutant in the receptor binding site of the B subunit of LT, the G33D mutant, has been reported to lack the immunological properties of the native B subunit [Nashar et al. (1996) PNAS 93:226], suggesting that binding to the receptor is important for the immunogenicity. It has also been shown that non-toxic derivatives of LT carrying mutant A subunits retain the immunological properties of wild-type LT [eg. Magagnoli et al. (1996) 64:5434], suggesting that ADP-ribosylation activity is not essential for immunogenicity.

In relation to adjuvanticity, much data has been generated but many questions remain unanswered. Some studies have suggested that LT-B and CT-B have adjuvant activity, but the conclusions drawn have been compromised by contamination with active toxin [Wilson et al. (1993) Vaccine 11:113]. Studies with recombinant LT-B and CT-B have suggested that they behave as poor mucosal adjuvants [eg. Douce et al. (1997) Infect. Immun. 65:2821]

Attempts to define the role of ADP-ribosylation activity in the adjuvanticity of LT has generated conflicting results. Lycke et al. [Eur J Immunol (1992) 22:2277] have described a non-toxic LT derivative (LT-E112K) which, when administered with KLH by oral route in mice, lacked the adjuvant properties of wild-type LT, thus suggesting that adjuvant activity is linked to ADP-ribosylation activity. LT derivatives such as LT-K7 and LT-K63 [eg. Douce et al. (1997) supra; Douce et al. (1996) PNAS 92:1644; DiTommaso et al. (1996) Infect Immun 64:974], however, which are devoid of toxicity both in vitro and in vivo, have been shown to be able to elicit an antibody response against a co-administered antigen in intranasally immunised mice. LT-K63 has been shown to induce measle-specific CTL response after intranasal immunisation with a synthetic peptide [Partidos et al. (1996) Immunol 89:483], and strongly enhances protection against H. pylori following intragastric immunisation with H. pylori antigens. The antibody titres induced by these non-toxic LT mutants were lower than those obtained with wild-type toxin, however, and were only detected after two mucosal immunisations [Douce et al. (1997) supra].

It is an object of the invention to provide forms of LT which are detoxified, so that they might be suitable for use in humans, but which retain the adjuvant and immunogenic properties of LT as far as possible.

SUMMARY OF THE INVENTION

According to a first aspect of the present invention, there is provided an immunogenic detoxified protein comprising the amino acid sequence of subunit A of an E. coli heat labile toxin (LT-A), or a fragment thereof, wherein at least amino acid Ala-72 in said sequence or fragment is mutated.

As used herein, the term "detoxified" means that the toxoid exhibits a reduction in toxicity relative to the wild-type toxin. The toxicity may be measured in mouse cells, CHO cells, by evaluation of the morphological changes induced in Y1 cells, or preferably by the rabbit ileal loop assay. As measured in Y1 cells, for instance, "detoxified" means that the toxoid exhibits a reduction in toxicity relative to the wild-type toxin of greater than 10,000-fold.

Any residual toxicity should be sufficiently low for the protein to be used in an effective immunogenic composition without causing significant side effects. Certain mutants within the scope of the invention may possess zero toxic activity.

As used herein, the term "residual toxicity" means that the detoxified immunogenic protein may retain a measurable toxicity. More particularly the level of toxicity may be optimised in a benefit/side-effect trade-off to maximise immunogenicity and/or adjuvanticity whilst maintaining a sufficiently low toxicity to be tolerated by the subject after administration.

Thus, although these proteins are detoxified in the sense of having a much lower toxicity than the wild-type protein, traces of the enzymatic activity responsible for toxicity may remain. The mutation causes a decrease in toxicity of which makes the toxoid suitable for human use.

Most preferably the toxicity of the toxoid is reduced relative to its natural occurring counterpart by greater than 10,000 fold as measured by the evaluation of the morphological changes induced in Y1 cells or greater than 10 fold as measured by the rabbit ileal loop assay, performed as described herein.

The term "toxoid" as used herein means a detoxified mutated toxin protein.

In this specification, references to LT encompass the various naturally occurring strain variants as well other variants encompassing mutations which do not significantly alter the properties of the subunits or of the assembled holotoxin. These mutations may be, for instance, conservative amino acid changes which do not affect the assembly of the holotoxin.

References to LT-A also encompass fragments of LT-A provided that the fragment contains Ala-72.

Most importantly, the toxoid must remain immunologically cross-reactive with the toxin from which it is derived.

The immunogenic protein may be LT subunit A toxoid, but is preferably an assembled holotoxoid comprising a LT-A toxoid and five LT-B subunits, which may themselves be wild-type or mutated.

It will be appreciated that in derivatives of LT-A, such as fragments, or in LT-A proteins of different $E.$ $coli$ strains, the amino acid residue to be mutated is that which corresponds to Ala-72 as defined for LT-A in Domenighini et al. [Molec. Microbiol. (1995) 15:1165–1167]. Ala-72 is located on the second turn of the alpha-helix in LT-A and faces the NAD binding site. An alignment of amino acid sequence entries for enterotoxin A subunits is shown in FIG. 1 of Domenighini and reproduced as FIG. 12 herein. The correct sequences of LTp, LTh LT-IIa and LT-IIb as given in Domenighini are as follows:

LTp:
NGDRLYRADSRPPDEIKRSGGLMPRGH-
  NEYFDROTOMNINLYDHARGTQTGFVRY
  DDGYVSTSLSLRSAHLAGOSILSGY-
  STYYIYVIATAPNMFNVNDVLGVYSPHPYEOE
  VSALGGIPYSQIYGWYRVNFGVIDER-
  LHRNREYRDRYYRNLNIAPAEDGYRLAGFP
  PDHOAWREEPWIHHAPOGCGNSSRTIT-
  GDTCNEETONLSTIYLREYOSKVKROIFSD
  YQSEVDIYNRIRDEL (SEQ ID NO:1)
LTh:
NGDKLYRADSRPPDEIKRSGGLMPRGH-
  NEYFDROTOMNINLYDHARGTOTGFVRY
  DDGYVSTSLSLRSAHLAGOSILSGY-
  STYYIYVIATAPNMFNVNDVLGVYSPHPYEQE
  VSALGGIPYSQIYGWYRVNFGVIDER-
  LHRNREYRDRYYRNLNIAPAEDGYRLAGFP
  PDHQAWREEPWIHHAPQGCGNSSRTIT-
  GDTCNEETONLSTIYLRKYQSKVKRQIFSD
  YQSEVDIYNRIRNEL (SEQ ID NO:2)

LT-IIa:
NDFFRADSRTPDEIRRAGGLL-
  PRGQOEAYERQTPININLYEHARGTVT-
  GNTRYNDG   YVSTTVTLRQAHLIGONILGSYN-
  EYYIYVVAPAPNLFDVNGVLGRYSPYPSENEFAA
  LGGIPLSQIIGWYRVSFGAIEGGMQRN-
  RDYRGDLFRGLTVAPNEDGYQLAGFPSNFP
  AWREMPWSTFAPEOCVPNNKEFKGGVCI-
  SATNVLSKYDLMNFKKLLKRRLALTFF   MSED-
  DFIGVHGERDEL (SEQ ID NO:3)
LT-IIb:
NDYFRADSRTPDEVRRSGGLIPR-
  GODEAYEROTPININLYDHARGTATGNTRYNDG
  YVSTTTTLROAHFLGONMLGGYNEYY-
  IYVVAAAPNLFDVNGVLGRYSPYPSENEF AALG-
  GIPLSOIIGWYRVSFGAIEGGMHRN-
  RDYRRDLFRGLSAAPNEDGYRIAGFPDG
  FPAWEEVPWREFAPNSCLPNNKASSDT-
  TCASLTNKLSOHDLADFKKYIKRKFTLMR
  INNDGFFSNNGGKDEL (SEQ ID NO:4)

The mutation at Ala-72 may be a substitution, an insertion, or a deletion. Preferably it is a substitution with a different amino acid. The most preferred mutation is the substitution of Ala-72 with arginine, for which the standard nomenclatur is A72R.

Whilst the A72R mutant retains residual toxicity, other mutants within the scope of the invention may possess no toxicity, for example mutants with one or more mutations at other sites, or toxoids which are further detoxified by chemical means.

The or each amino acid substituted for a wild type amino acid, whether at Ala-72 or elsewhere, may be a naturally occurring amino acid or may be a modified or synthetic amino acid, provided that the mutant retains the necessary immunogenic and detoxified properties.

Substitutions which alter the amphotericity and/or hydrophilicity of the protein whilst retaining as far as possible the steric effect of the substituted amino acid are generally preferred.

The toxoids of the invention may be synthesised chemically using conventional peptide synthesis techniques, but are preferably produced by recombinant DNA means.

Preferably the toxoid is obtained in substantially pure form.

According to a second aspect of the invention, there is provided an immunogenic composition comprising an immunogenic detoxified protein of the first aspect of the invention and a pharmaceutically acceptable carrier. This immunogenic composition may be a vaccine against the enterotoxigenic strains of $E.$ $coli$ itself and may thus optionally further comprise an adjuvant.

In addition to the properties typical of mutants devoid of enzymatic activity, the mutant proteins also exhibit adjuvant activity.

Additionally, the immunogenic composition may further comprise a second antigen capable of raising an immunological response to another disease. In such an alternative composition, the immunogenic detoxified protein of the invention can act as a mucosal adjuvant.

According to a third aspect of the invention, there is provided the use of a toxoid of the first aspect as an adjuvant.

According to a fourth aspect of the invention, there is provided a method of vaccinating a mammal against an enterotoxigenic strain of $E.$ $coli$ comprising administering an immunologically effective amount of an immunogenic detoxified protein according to the first aspect of the invention. Optionally, the immunogenic detoxified protein of the invention may act as an adjuvant for a second immunogenic protein administered separately, sequentially or with the immunogenic detoxified protein of the invention.

According to a fifth aspect of the invention, there is provided a DNA sequence encoding an immunogenic detoxified protein according to the first aspect of the invention.

Preferably the DNA sequence encodes both the detoxified subunit A and subunit B in a polycistronic unit. Alternatively, the DNA may encode only the detoxified subunit A.

According to a sixth aspect of the invention, there is provided a vector comprising a DNA sequence according to the fifth aspect of the invention.

According to a seventh aspect of the invention, there is provided a host cell transformed with a vector according to the sixth aspect of the invention.

The host cell may be any host capable of expressing a DNA sequence according to the fifth aspect, but is preferably a bacterium, most preferably E. coli, suitably transfected to produce the desired immunogenic detoxified protein.

In a further embodiment of the seventh aspect of the invention, the host cell may itself provide a protective species, for example an E. coli strain mutated to a phenotype lacking wild type LT and expressing an immunogenic detoxified protein of the first aspect of the invention.

According to a eighth aspect of the invention, there is provided a process for the production of an immunogenic detoxified protein according to the first aspect of the invention comprising culturing a host cell according to the seventh aspect of the invention.

According to a ninth aspect of the invention, there is provided a process for the production of DNA according to the fifth aspect of the invention comprising the steps of subjecting a DNA encoding a wild-type LT-A or a fragment thereof to site-directed mutagenesis.

According to a tenth aspect of the invention, there is provided a process for the formulation of an immunogenic composition according to the second aspect comprising bringing an immunogenic detoxified protein according to the first aspect of the invention into association with a pharmaceutically acceptable carrier, and optionally with an adjuvant.

According to a eleventh aspect of the invention, there is provided a method for the prevention or treatment of disease in a subject, comprising administering to said subject an immunologically effective dose of an immunogenic composition according to the second aspect.

INDUSTRIAL APPLICABILITY

The immunogenic detoxified protein of the invention may constitute the active component of a vaccine composition useful for the prevention and treatment of infections by enterotoxigenic strains of E. coli. The immunogenic detoxified protein may also be used in a vaccine composition as a mucosal adjuvant. The compositions are thus applicable for use in the pharmaceutical industry.

DESCRIPTION OF THE DRAWINGS

FIG. 1 is a chromatographic profile on a superdex column, with peak I corresponding to holotoxin and peak II to the EDTA in the buffer; FIG. 2 is a Western blot of a trypsin digest experiment; FIG. 3 shows the reults of in vitro ADP-ribosylation of polyarginine; and FIGS. 4 and 5 show the results of in vitro and in vivo toxicity experiments, respectively.

FIG. 12 (SEQ ID NOs:1 through 4) is an alignment of amino acid sequences of wild-type LT-A. SEQ ID NO:1 shows a wild-type sequence of a porcine LT. SEQ ID NO:2 shows a wild-type sequence of a human LT. SEQ ID NO:3 and SEQ ID NO:4 show wild-type sequences of two variants of human Type II LT, designated IIa and IIb, respectively. Dashes indicate identical residues as compared to SEQ ID NO:1. Gaps introduced to maximize alignments are shown by periods.

DETAILED DESCRIPTION OF EMBODIMENTS OF THE INVENTION

Figure 1:
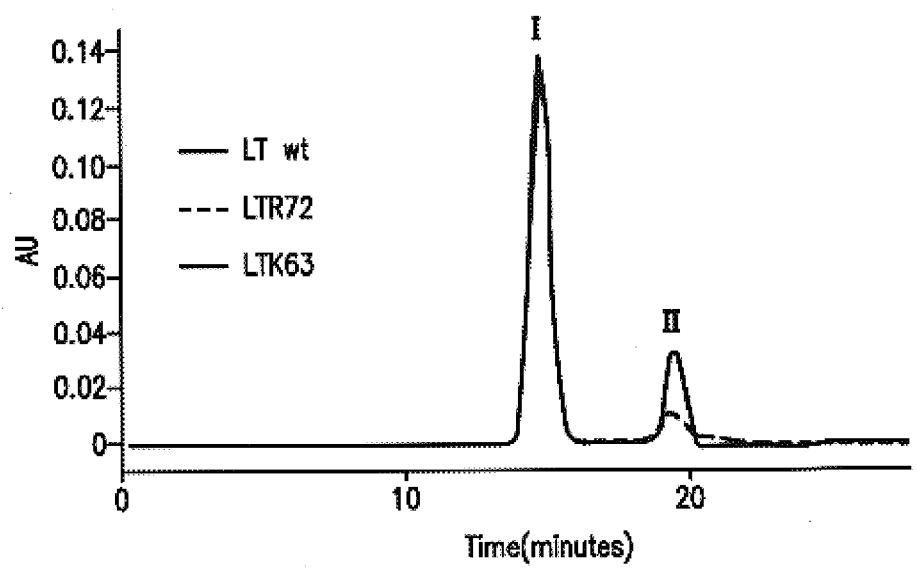
FIGS. 1 to 5 show the biochemical and biological properties of wild-type LT and of mutants LT-A72R (also shown as "LTR72") and LTK63.
Figure 2:
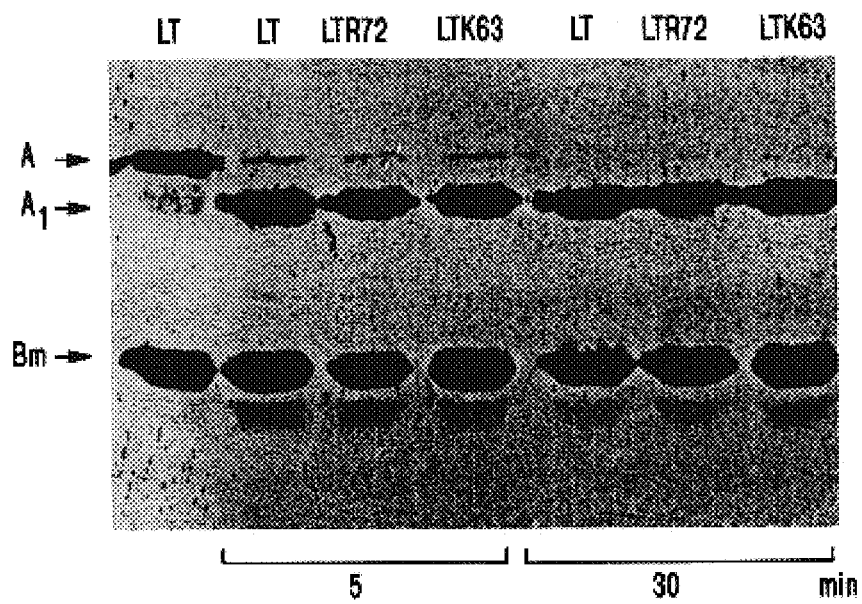
Figure 4:
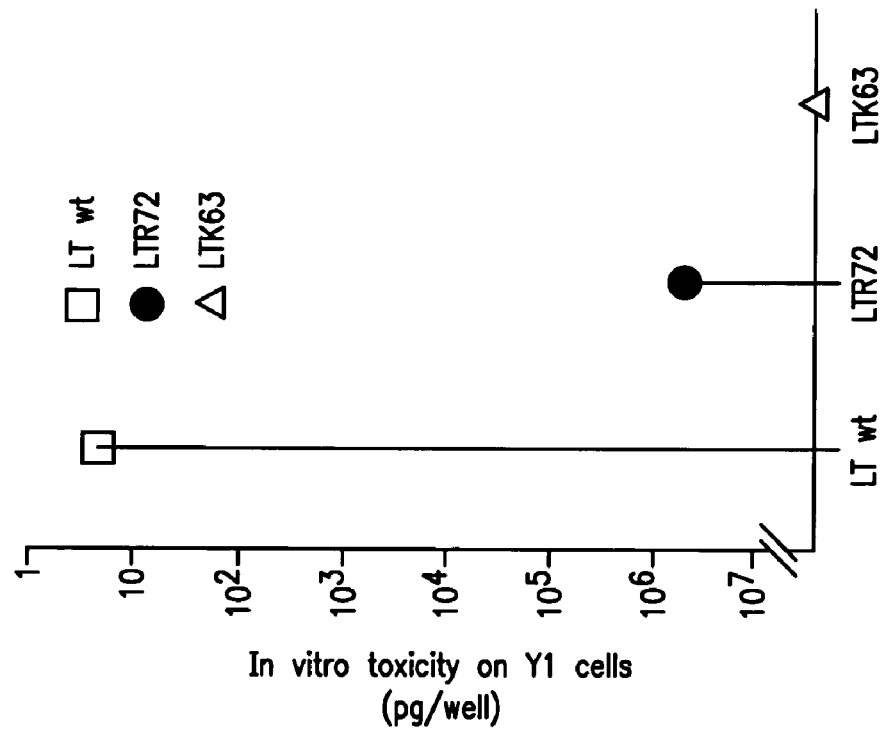
Figure 3:
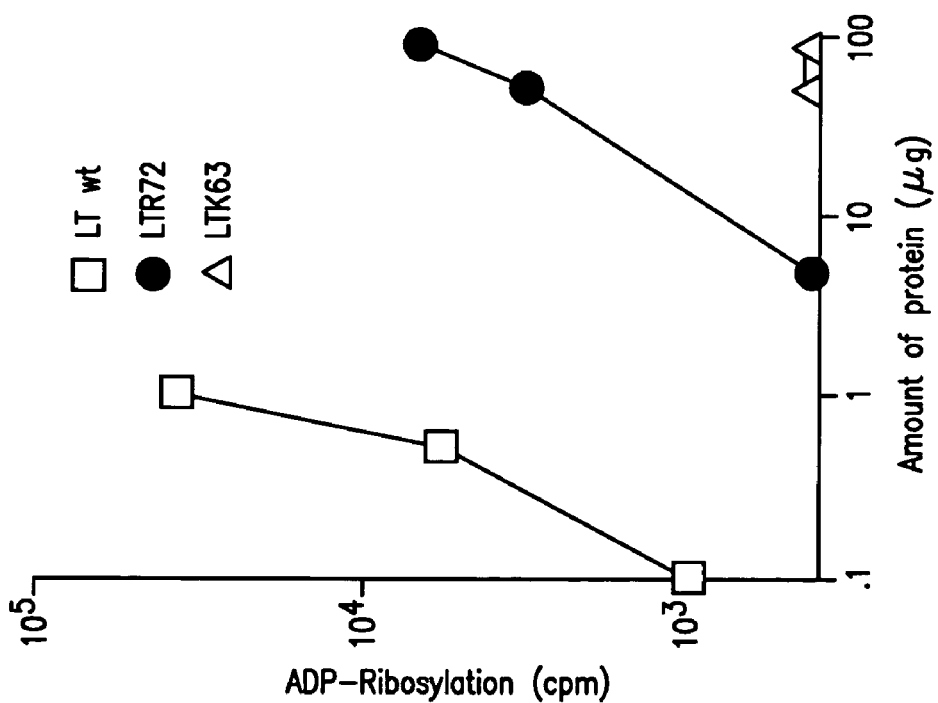
Figure 5:
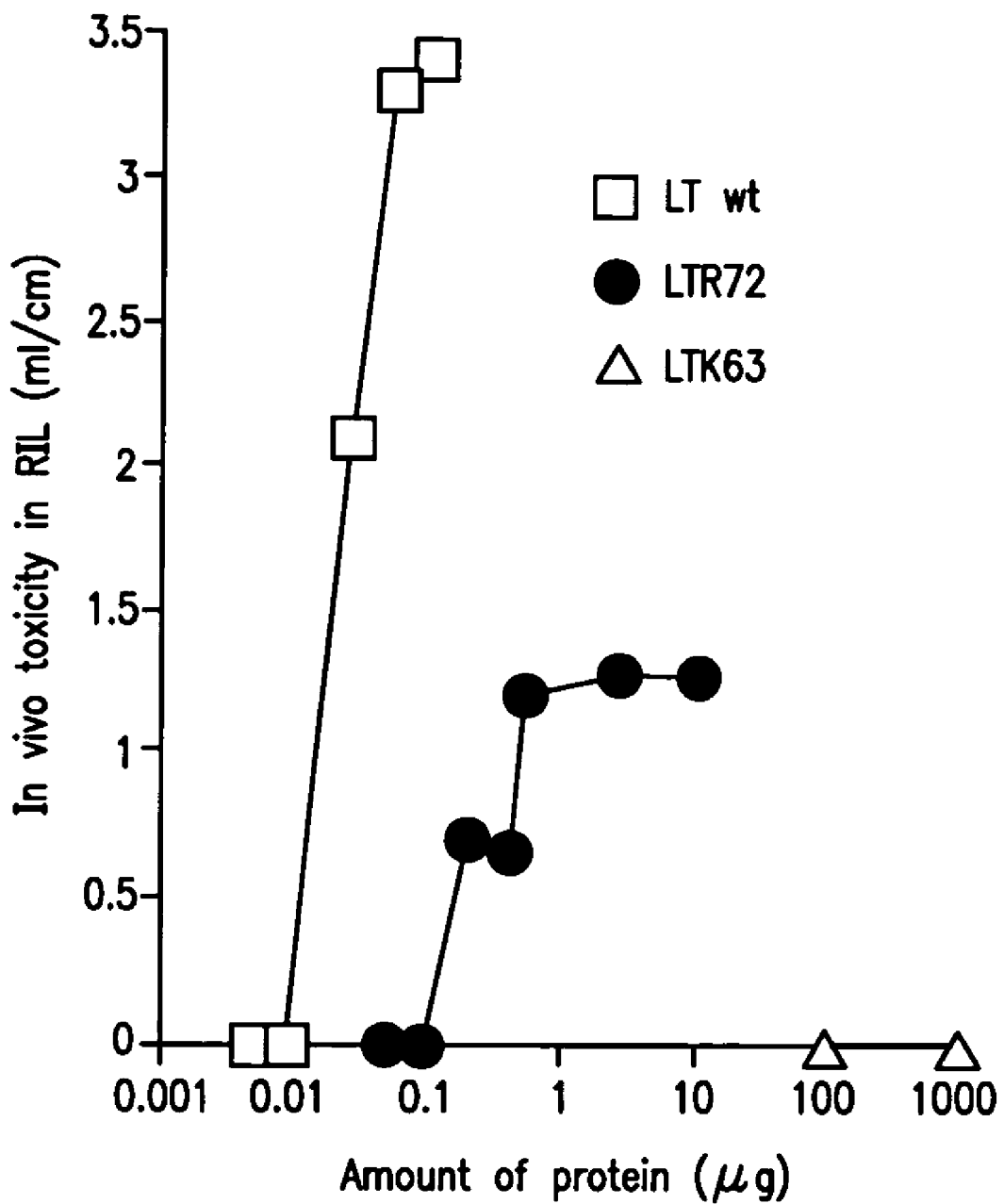

The practice of the present invention will employ, unless otherwise indicated, conventional techniques of molecular biology, microbiology, recombinant DNA, and immunology, which are within the skill of the art. Such techniques are explained fully in the literature. See eg., Sambrook, et al., MOLECULAR CLONING; A LABORATORY MANUAL, SECOND EDITION (1989); DNA CLONING, VOLUMES I AND II (D. N Glover ed. 1985); OLIGONUCLEOTIDE SYNTHESIS (M. J. Gait ed, 1984); NUCLEIC ACID HYBRIDIZATION (B. D. Hames & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS IN ENZYMOLOGY (Academic Press, Inc.); GENE TRANSFER VECTORS FOR MAMMALIAN CELLS (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker, eds. (1987), IMMUNOCHEMICAL METHODS IN CELL AND MOLECULAR BIOLOGY (Academic Press, London), Scopes, (1987), PROTEIN PURIFICATION: PRINCIPLES AND PRACTICE, Second Edition (Springer-Verlag, N.Y.), and HANDBOOK OF EXPERIMENTAL IMMUNOLOGY, VOLUMES I–IV (D. M. Weir and C. C. Blackwell eds 1986).

Standard abbreviations for nucleotides and amino acids are used in this specification. All publications, patents, and patent applications cited herein are incorporated by reference.

In particular, the following amino acid abbreviations are used:

| Alanine | A | Ala | Arginine | R | Arg |
|---|---|---|---|---|---|
| Asparagine | N | Asn | Aspartic Acid | D | Asp |
| Cysteine | C | Cys | Glycine | G | Gly |
| Glutamic Acid | E | Glu | Glutamine | Q | Gln |
| Histidine | H | His | Isoleucine | I | Ile |
| Leucine | L | Leu | Lysine | K | Lys |
| Methionine | M | Met | Phenylalanine | F | Phe |
| Proline | P | Pro | Serine | S | Ser |
| Threonine | T | Thr | Tryptophan | W | Trp |
| Tyrosine | Y | Tyr | Valine | V | Val |

As mentioned above examples of the immunogenic detoxified protein that can be used in the present invention include polypeptides with minor amino acid variations from the natural amino acid sequence of the protein other than at the sites of mutation specifically mentioned.

A significant advantage of producing the immunogenic detoxified protein by recombinant DNA techniques rather than by isolating and purifying a protein from natural sources is that equivalent quantities of the protein can be produced by using less starting material than would be required for isolating the protein from a natural source. Producing the protein by recombinant techniques also permits the protein to be isolated in the absence of some molecules normally present in cells. Indeed, protein compositions entirely free of any trace of human protein contaminants cad readily be produced because the only human protein produced by the recombinant non-human host is the recombinant protein at issue. Potential viral agents from natural sources and viral components pathogenic to humans are also avoided. Also, genetically detoxified toxin are less likely to revert to a toxic from than more traditional, chemically detoxified toxins.

Pharmaceutically acceptable carriers include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes) and inactive virus particles. Such carriers are well known to those of ordinary skill in the art. Additionally, these carriers may function as immunostimulating agents (adjuvants).

Preferred aditional adjuvants to enhance effectiveness of immunogenic compositions include, but are not limited to: aluminum salts (alum) such as aluminium hydroxide, aluminium phosphate, aluminium sulfate etc, oil emulsion formulations, with or without other specific immunostimulating agents such as muramyl peptides or bacterial cell wall components, such as for example (1) MF59 (Published International patent application WO90/14837, containing 5% Squalene, 0.5% Tween® 80, 0.5% Span® 85 (optionally containing various amounts of MTP-PE (see below), although not required) formulated into submicron particles using a microfluidizer such as Model 110Y microfluidizer (Microfluidics, Newton, Mass. 02164), (2) SAF, containing 10% squalene, 0.4% Tween 80, 5% pluronic-blocked polymer L121, and thr-MDP (see below) either microfluidized into a submicron emulsion or vortexed to generate a larger particle size emulsion, and (3) RIBI™ adjuvant system (RAS) (Ribi Immunochem, Hamilton, Mont.) containing 2% Squalene, 0.2% Tween® 80 and one or more bacterial cell wall components from the group consisting of monophosphoryl lipid A (MPL), trehalose dimycolate (TDM), and cell wall skeleton (CWS) preferably MPL+CWS (Detox™), muramyl peptides such as N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE) etc., and cytokines, such as interleukins (IL-1, IL-2 etc) macrophage colony stimulating factor (M-CSF), tumour necrosis factor (TNF) etc. Additionally, saponin adjuvants, such as Stimulon™ (Cambridge Bioscience, Worcester, Mass.) may be used or particles generated therefrom such as ISCOMS (immunostimulating complexes). Furthermore, Complete Freunds Adjuvant (CFA) and Incomplete Freunds Adjuvant (IFA) may be used. Alum and MF59 are preferred.

The immunogenic-detoxified protein of the invention may be used as an adjuvant for a second antigen in an immunologically active composition for the treatment or vaccination of the human or animal body.

The immunogenic compositions (eg the antigen, pharmaceutically acceptable carrier and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect as discussed above under pharmaceutically acceptable carriers.

Immunogenic compositions used as vaccines comprise an immunologically effective amount of the antigenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (eg., nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, eg. by injection either subcutaneously or intramuscularly. Additional formulations suitable for other modes of administration include oral and pulmonary formulations, suppositories and transdermal applications. Dosage treatment may be a single dose schedule or a multiple dose schedule. The vaccine may be administered in conjunction with other immunoregulatory agents.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (eg., methyl phosphonates, phosphotriesters, phosphoamidates, carbamates, etc.) and with charged linkages (eg., phosphorothioates, phosphorodithioates, etc.), those containing pendant moieties, such as, for example proteins (including for eg., nucleases, toxins, antibodies, signal peptides, poly-L-lysine, etc.), those with intercalators (g., acridine, psoralen, etc.), those containing chelators (eg., metals, radioactive metals, boron, oxidative metals, etc.), those containing alkylators, those with modified linkages (eg., alpha anomeric nucleic acids, etc.), as well as unmodified forms of the polynucleotide.

A "replicon" is any genetic element, eg., a plasmid, a chromosome, a virus, a cosmid, etc. that behaves as an autonomous unit of polynucleotide replication within a cell; i.e., capable of replication under its own control. This may include selectable markers.

A "vector" is a replicon in which another polynucleotide segment is attached, so as to bring about the replication and/or expression of the attached segment.

"Control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is necessary for expression, and may also include additional components whose presence is advantageous, for example, leader sequences and fusion partner sequences.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide; this region may represent a portion of a coding sequence or a total coding sequence.

A "coding sequence" is a polynucleotide sequence which is translated into a polypeptide, usually via mRNA, when placed under the control of appropriate regulatory sequences. The boundaries of the coding sequence are determined by a translation start codon at the 5'-terminus and a translation stop codon at the 3'-terminus. A coding sequence can include, but is not limited to, cDNA, and recombinant polynucleotide sequences.

"PCR" refers to the technique of polymerase chain reaction as described in Saiki, et al., Nature 324:163 (1986); and Scharf et al., Science (1986) 233:1076–1078; and U.S. Pat. No. 4,683,195; and U.S. Pat. No. 4,683,202.

As used herein, x is "heterologous" with respect to y if x is not naturally associated with y in the identical manner; i.e., x is not associated with y in nature or x is not associated with y in the same manner as is found in nature.

"Homology" refers to the degree of similarity between x and y. The correspondence between the sequence from one form to another can be determined by techniques known in the art. For example, they can be determined by a direct comparison of the sequence information of the polynucleotide. Alternatively, homology can be determined by hybridization of the polynucleotides under conditions which form stable duplexes between homologous regions (for example, those which would be used prior to $S_1$ digestion), followed by digestion with single-stranded specific nuclease(s), followed by size determination of the digested fragments.

As used herein, the term "polypeptide" refers to a polymer of amino acids and does not refer to a specific length of the product; thus, peptides, oligopeptides, and proteins are included within the definition of polypeptide. This term also does not refer to or exclude post expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

A polypeptide or amino acid sequence "derived from" a designated nucleic acid sequence refers to a polypeptide having an amino acid sequence identical to that of a polypeptide encoded in the sequence, or a portion thereof wherein the portion consists of at least 3–5 amino acids, and more preferably at least 8–10 amino acids, and even more preferably at least 11–15 amino acids, or which is immunologically identifiable with a polypeptide encoded in the sequence. This terminology also includes a polypeptide expressed from a designated nucleic acid sequence.

The protein may be used for producing antibodies, either monoclonal or polyclonal, specific to the protein. The methods for producing these antibodies are known in the art.

"Recombinant host cells", "host cells," "cells," "cell cultures," and other such terms denote, for example, microorganisms, insect cells, and mammalian cells, that can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation. Examples for mammalian host cells include Chinese hamster ovary (CHO) and monkey kidney (COS) cells.

Specifically, as used herein, "cell line," refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. The term "cell lines" also includes immortalized cells. Preferably, cell lines include nonhybrid cell lines or hybridomas to only two cell types.

As used herein, the term "microorganism" includes prokaryotic and eukaryotic microbial species such as bacteria and fungi, the latter including yeast and filamentous fungi.

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host genome.

By "genomic" is meant a collection or library of DNA molecules which are derived from restriction fragments that have been cloned in vectors. This may include all or part of the genetic material of an organism.

By "cDNA" is meant a complementary DNA sequence that hybridizes to a complementary strand of DNA.

By "purified" and "isolated" is meant, when referring to a polypeptide or nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type present (but water, buffers, and other small molecules, especially molecules having a molecular weight of less than 1000, can be present).

Once the appropriate coding sequence is isolated, it can be expressed in a variety of different expression systems; for example those used with mammalian cells, baculoviruses, bacteria, and yeast.

i. Mammalian Systems

Mammalian expression systems are known in the art. A mammalian promoter is any DNA sequence capable of binding mammalian RNA polymerase and initiating the downstream (3') transcription of a coding sequence (eg. structural gene) into mRNA. A promoter will have a transcription initiating region, which is usually placed proximal to the 5' end of the coding sequence, and a TATA box, usually located 25–30 base pairs (bp) upstream of the transcription initiation site. The TATA box is thought to direct RNA polymerase II to begin RNA synthesis at the correct site. A mammalian promoter will also contain an upstream promoter element, usually located within 100 to 200 bp upstream of the TATA box. An upstream promoter element determines the rate at which transcription is initiated and can act in either orientation [Sambrook et al. (1989) "Expression of Cloned Genes in Mammalian Cells." In *Molecular Cloning: A Laboratory Manual, 2nd ed.*].

Mammalian viral genes are often highly expressed and have a broad host range; therefore sequences encoding mammalian viral genes provid particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallotheionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter [Maniatis et al. (1987) *Science* 236:1237; Alberts et al. (1989) *Molecular Biology of the Cell,* 2nd ed.]. Enhancer elements derived from viruses may be particularly useful, because they usually have a broader host range. Examples include the SV40 early gene enhancer [Dijkema et al (1985) *EMBO J.* 4:761] and the enhancer/promoters derived from the long terminal repeat (LTR) of the Rous Sarcoma Virus [Gorman et al. (1982b) *Proc. Natl. Acad. Sci.* 79:6777] and from human cytomegalovirus [Boshart et al. (1985) *Cell* 41:521]. Additionally, some enhancers are regulatable and become active only in the presence of an inducer, such as a hormone or metal ion [Sassone-Corsi and Borelli (1986) *Trends Genet.* 2:215; Maniatis et al. (1987) *Science* 236:1237].

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus triparite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation [Birnstiel et al. (1985) *Cell* 41:349; Proudfoot and Whitelaw (1988) "Termination and 3' end processing of eukaryotic RNA. In *Transcription and splicing* (ed. B. D. Hames and D. M. Glover); Proudfoot (1989) *Trends Biochem. Sci.* 14:105]. These sequences direct the transcription of an mRNA which can be translated into the polypeptide encoded by the DNA. Examples of transcription terminater/polyadenylation signals include those derived from SV40 [Sambrook et al (1989) "Expression of cloned genes in cultured mammalian cells." In *Molecular Cloning: A Laboratory Manual*].

Some genes may be expressed more efficiently when introns (also called intervening sequences) are present. Several cDNAs, however, have been efficiently expressed from vectors that lack splicing signals (also called splice donor and acceptor sites) [see eg., Gothing and Sambrook (1981) *Nature* 293:620]. Introns are intervening noncoding sequences within a coding sequence that contain splice donor and acceptor sites. They are removed by a process called "splicing," following polyadenylation of the primary transcript [Nevins (1983) *Annu. Rev. Biochem.* 52:441; Green (1986) *Annu. Rev. Genet.* 20:671; Padgett et al. (1986) *Annu. Rev. Biochem.* 55:1119; Krainer and Maniatis (1988) "RNA splicing." In *Transcription and splicing* (ed. B. D. Hames and D. M. Glover)].

Usually, the above described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (eg., plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 [Gluzman (1981) *Cell* 23:175] or polyomavirus, replicate to extremely high copy number in the presence of the appropriate viral T antigen. Additional examples of mammalian replicons include those derived from bovine papillomavirus and Epstein-Barr virus. Additionally, the replicon may have two replication systems, thus allowing it to be maintained, for example, in mammalian cells for expression and in a procaryotic host for cloning and amplification. Examples of such mammalian-bacteria shuttle vectors include pMT2 [Kaufman et al. (1989) *Mol. Cell. Biol.* 9:946 and pHEBO [Shimizu et al. (1986) *Mol. Cell. Biol.* 6:1074].

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (eg., Hep G2), and a number of other cell lines.

ii. Baculovirus Systems

The polynucleotide encoding the protein can also be inserted into a suitable insect expression vector, and is operably linked to the control elements within that vector. Vector construction employs techniques which are known in the art.

Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif. ("MaxBac" kit). These techniques are generally known to those skilled in the art and fully described in Summers and Smith, *Texas Agricultural Experiment Station Bulletin No.* 1555 (1987) (hereinafter "Summers and Smith").

Prior to inserting the DNA sequence encoding the protein into the baculovirus genome, the above described components, comprising a promoter, leader (if desired), coding sequence of interest, and transcription termination sequence, are usually assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (eg., plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, *Virology* (1989) 17:31.

The plasmid usually also contains the polyhedrin polyadenylation signal (Miller et al. (1988) *Ann. Rev. Microbiol.*, 42:177) and a procaryotic ampicillin-resistance (amp) gene and origin of replication for selection and propagation in *E. coli.*

Baculovirus transfer vectors usually contain a baculovirus promoter. A baculovirus promoter is any DNA sequence capable of binding a baculovirus RNA polymerase and initiating the downstream (5' to 3') transcription of a coding sequence (eg. structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in: *The Molecular Biology of Baculoviruses* (ed. Walter Doerfler); EPO Publ. Nos. 127 839 and 155 476; and the gene encoding the p10 protein, Vlak et al., (1988), *J. Gen. Virol.* 69:765.

DNA encoding suitable signal sequences can be derived from genes for secreted insect or baculovirus proteins, such as the baculovirus polyhedrin gene (Carbonell et al. (1988) *Gene,* 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon, Maeda et al., (1985), *Nature* 315:592; human gastrin-releasing peptide, Lebacq-Verheyden et al., (1988), *Molec. Cell. Biol.* 8:3129; human IL-2, Smith et al., (1985) *Proc. Nat'l Acad. Sci. USA,* 82:8404; mouse IL-3, (Miyajima et al., (1987) *Gene* 58:273; and human glucocerebrosidase, Martin et al. (1988) *DNA,* 7:99, can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2–5 kb section of the baculovirus genome. Methods for introducing heterologous DNA into the desired site in the baculovirus virus are known in the art. (See Summers and Smith supra; Ju et al. (1987); Smith et al., *Mol. Cell. Biol.* (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), *Bioessays* 4:91. The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 μm in size, are highly refractile, giving them a bright shiny appearance that is readily visualized under the light microscope. Cells infected with recombinant viruses lack occlusion bodies. To distinguish recombinant virus from wild-type virus, the transfection supernatant is plagued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al. eds) at 16.8 (Supp. 10, 1990); Summers and Smith, supra; Miller et al. (1989).

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodoptera frugiperda,* and *Trichoplusia ni* (PCT Pub. No. WO 89/046699; Carbonell et al., (1985) *J. Virol.* 56:153; Wright (1986) *Nature* 321:718; Smith et al., (1983) *Mol. Cell. Biol.* 3:2156; and see generally, Fraser, et al. (1989) *In Vitro Cell. Dev. Biol.* 25:225).

Cells and cell culture media are commercially available for both direct and fusion expression of heterologous polypeptides in a baculovirus/expression system; cell culture technology is generally known to those skilled in the art. See, eg., Summers and Smith [supra].

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, eg., HPLC, affinity chromatography, ion exchange chromatography, etc.; electrophoresis; density gradient centrifugation; solvent extraction, or the like. As appropriate, the product may be further purified, as required, so as to remove substantially any insect proteins which are also secreted in the medium or result from lysis of insect cells, so as to provide a product which is at least substantially free of host debris, eg., proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

iii. Bacterial Systems

Bacterial expression techniques are known in the art. A bacterial promoter is any DNA sequence capable of binding bacterial RNA polymerase and initiating the downstream (3") transcription of a coding sequence (eg. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al. (1984) *Annu. Rev. Genet.* 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) *Nature* 198:1056], and maltose. Additional examples include promoter sequences derived from biosynthetic enzymes such as tryptophan (trp) (Goeddel et al. (1980) *Nuc. Acids Res.* 8:4057; Yelverton et al. (1981) *Nucl. Acids Res.* 9:731; U.S. Pat. No. 4,738,921; EPO Publ. Nos. 036 776 and 121 775].

The g-laotamase (bla) promoter system [Weissmann (1981) "The cloning of interferon and other mistakes." In *Interferon* 3 (ed. I. Gresser)], bacteriophage lambda PL [Shimatake et al. (1981) *Nature* 292:128] and T5 [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551, 433]. For example, the tac promoter is a hybrid trp-lac promoter comprised of both trp promoter and lac operon sequences that is regulated by the lac repressor [Amann et al. (1983) *Gene* 25:167; de Boer et al. (1983) *Proc. Natl. Acad. Sci.* 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophase T7 RNA polymerase/promoter system is an example of a coupled promoter system [Studier et al. (1986) *J. Mol. Biol.* 189:113; Tabor et al. (1985) *Proc Natl. Acad. Sci.* 82:1074]. In addition, a hybrid promoter can also be comprised of a bacteriophage promoter and an *E. coli* operator region (EPO Publ. No. 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3–9 nucleotides in length located 3–11 nucleotides upstream of the initiation codon [Shine et al. (1975) *Nature* 254:34]. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)]. To express eukaryotic genes and prokaryotic genes with weak ribosome-binding site [Sambrook et al. (1989) "Expression of cloned genes in *Escherichia coli*." In *Molecular Cloning: A Laboratory Manual]*.

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO Publ. No. 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene [Nagai et al. (1984) *Nature* 309:810]. Fusion proteins can also be made with sequences from the lacZ [Jia et al. (1987) *Gene* 60:197], trpE [Allen et al. (1987) J. Biotechnol. 5:93; Makoff et al. (1989) *J. Gen. Microbiol.* 135:11], and Chey [EPO Publ. No. 324 647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (eg. ubiquitin specific processing-protease) to cleave the ubiquitin from the foreign protein. Through this method, native foreign protein can be isolated [Miller et al. (1989) *Bio/Technology* 7:698].

Alternatively, foreign proteins can also be secreted from the cell by creating chimeric DNA molecules that encode a fusion protein comprised of a signal peptide sequence fragment that provides for secretion of the foreign protein in bacteria [U.S. Pat. No. 4,336,336]. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) [Masui et al. (1983), in: *Experimental Manipulation of Gene Expression*; Ghrayeb et al. (1984) *EMBO J.* 3:2437]and the *E. coli* alkaline phosphatase signal sequence (phoA) [Oka et al. (1985) *Proc. Natl. Acad. Sci.* 82:7212]. As an additional example, the signal sequence of the alpha-amylase gene from various *Bacillus* strains can be used to secrete heterologous proteins from *B. subtilis* [Palva et al. (1982) *Proc. Natl. Acad. Sci. USA* 79:5582; EPO Publ. No. 244 042].

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (eg., plasmids) capable of stable maintenance in a host, such as bacteria. The replicon will have a replication system, thus allowing it to be maintained in a procaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids.

Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various *Bacillus* strains integrate into the *Bacillus* chromosome (EPO Publ. No. 127 328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) *Annu. Rev. Microbiol.* 32:469]. Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable market that is either maintained in a replicon or developed into an integrating vector, as described above.

Expression and transformation vectors, either extrachromosomal replicons or integrating vectors, have been developed for transformation into many bacteria. For example, expression vectors have been developed for, inter alia, the following bacteria: *Bacillus subtilis* [Palva et al. (1982) *Proc. Natl. Acad. Sci. USA* 79:5582'; EPO Publ. Nos. 036 259 and 063 953; PCT Publ. No. WO 84/04541*], Escherichia coli* [Shimatake et al. (1981) *Nature* 292:128; Amann et al. (1985) *Gene* 40:183; Studier et al. (1986) *J. Mol. Biol.* 189:113; EPO Publ. Nos. 036 776, 136 829 and 136 907], *Streptococcus cremoris* [Powell et al. (1988) *Appl. Environ. Microbiol.* 54:655]; *Streptococcus lividans* [Powell et al. (1988) *Appl. Environ. Microbiol.* 54:655], *Streptomyces lividans* [U.S. Pat. No. 4,745,056].

Methods of introducing exogenous DNA into bacterial hosts are well-known in the art, and usually include either the transformation of bacteria treated with CaCl$_2$ or other agents, such as divalent cations and DMSO. DNA can also be introduced into bacterial cells by electroporation. Transformation procedures usually vary with the bacterial species to be transformed. See eg., [Masson et al. (1989) *FEMS Microbiol. Lett.* 60:273; Palva et al. (1982) *Proc. Natl. Acad. Sci. USA* 79:5582; EPO Publ. Nos. 036 259 and 063 953; PCT Publ. No. WO 84/04541, *Bacillus*], [Miller et al. (1988) *Proc. Natl. Acad. Sci.* 85:856; Wang et al. (1990) *J. Bacteriol.* 172:949, *Campylobacter*], [Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids. In *Genetic Engineering: Proceedings of the International Symposium on Genetic Engineering* (eds. H. W. Boyer and S. Nicosia); Mandel et al. (1970) *J. Mol. Biol.* 53:159; Taketo (1988) *Biochim. Biophys. Acta* 949:318; *Escherichia*], [Chassy et al. (1987) *FEMS Microbiol. Lett.* 44:173 *Lactobacillus*]; [Fiedler et al. (1988) *Anal. Biochem* 170:38, *Pseudomonas*]; [Augustin et al. (1990) *FEMS Microbiol. Lett.* 66:203, *Staphylococcus*], [Barany et al. (1980) *J. Bacteriol.* 144:698; Harlander (1987) "Transformation of *Streptococcus lactis* by electroporation, in: *Streptococcal Genetics* (ed. J. Ferretti and R. Curtiss III); Perry et al. (1981) *Infec. Immun.* 32:1295; Powell et al. (1988) *Appl. Environ. Microbiol.* 54:655; Somkuti et al. (1987) *Proc. 4th Evr. Cong. Biotechnology* 1:412, *Streptococcus*].

iv. Yeast Expression

Yeast expression systems are also known to one of ordinary skill in the art. A yeast promoter is any DNA sequence capable of binding yeast RNA polymerase and initiating the downstream (3') transcription of a coding sequence (eg. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EPO Publ. No. 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO Publ. No. 329 203). The yeast PHO5 gene, encoding acid phosphatase, also provides useful promoter sequences [Myanohara et al. (1983) *Proc. Natl. Acad. Sci. USA* 80:1].

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EPO Publ. No. 164 556). Furthermore, a yeast promoter can include naturally occurring promoters of non-yeast origin that have the ability to bind yeast RNA polymerase and initiate transcription. Examples of such promoters include, inter alia, [Cohen et al. (1980) *Proc. Natl. Acad. Sci. USA* 77:1078; Henikoff et al. (1981) *Nature* 283:835; Hollenberg et al. (1981) *Curr. Tonics Microbiol. Immunol.* 96:119; Hollenberg et al. (1979) "The Expression of Bacterial Antibiotic Resistance Genes i the Yeast *Saccharomyces cerevisiae*," in: *Plasmids of Medical. Environmental and Commercial Importance* (eds. K>N> Timmis and A. Puhler); Mercerau-Puigalon et al. (1980) *Gene* 11:163; Panthier et al. (1980) *Curr. Genet.* 2:109;].

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See eg., EPO Publ. No. 196 056. Another example is a ubiquitin fusion protein. Such a fusion protein is made with the ubiquitin region that preferably retains a site for a processing enzyme (eg. ubiquitin-specific processing protease) to cleave the ubiquitin from the foreign protein. Through this method, therefore, native foreign protein can be isolated (see, eg., PCT Publ. No. WO 88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EPO Publ. No. 012 873; JPO Publ. No. 62,096,086) and the A-factor gene (U.S. Pat. No. 4,588,684). Alternatively, leaders of non-yeast origin, such as an interferon leader, exist that also provide for secretion in yeast (EPO Publ. No. 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. Nos. 4,546,083 and 4,870,008; EPO Publ. No. 324 274). Additional leaders employing an alpha-factor leader fragment that provides for secretion include hybrid alpha-factor leaders made with a presequence of a first yeast, but a pro-region from a second yeast alphafactor. (See eg., PCT Publ. No. WO 89/02463.)

Usually, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Usually, the above described components, comprising a promoter, leader (if desired), coding sequence of interest, and transcription termination sequence, are put together into expression constructs. Expression constructs are often maintained in a replicon, such as an extrachromosomal element (eg., plasmids) capable of stable maintenance in a host, such as yeast or bacteria. The replicon may have two replication systems, thus allowing it to be maintained, for example, in yeast for expression and in a procaryotic host for cloning and amplification. Examples of such yeast-bacteria shuttle vectors include YEp24 [Botstein et al. (1979) Gene 8:17–24], pCl/1 [Brake et al. (1984) Proc. Natl. Acad. Sci USA 81:4642–4646], and YRp17 [Stinchcomb et al. (1982) J. Mol. Biol. 158:157]. In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. Enter a high or low copy number vector may be selected, depending upon the effect of the vector and the foreign protein on the host. See eg., Brake et al., supra.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al. (1983) Methods in Enzymol. 101:228–245]. An integrating vector may be directed to a specific locus in yeast by selecting the appropriate homologous sequence for inclusion in the vector. See Orr-Weaver et al., supra. One or more expression construct may integrate, possibly affecting levels of recombinant protein produced [Rine et al. (1983) Proc. Natl. Acad. Sci. USA 80:6750]. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al. (1987) Microbiol. Rev. 51:351].

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: Candida albicans [Kurtz, et al. (1986) Mol. Cell. Biol. 6:142], Candida maltose [Kunze, et al. (1985) J. Basic Microbiol. 25:141]. Hansenula polymorpha [Gleeson, et al. (1986) J. Gen. Microbiol. 132:3459; Roggenkamp et al. (1986) Mol. Gen. Genet. 202:302], Kluyveromyces fragilis [Das, et al. (1984) J. Bacteriol. 158:1165], Kluyveromyces lactis [De Louvencourt et al. (1983) J. Bacteriol. 154:737; Van den Berg et al. (1990) Bio/Technology 8:135], Pichia guillerimondii [Kunze et al. (1985) J. Basic Microbiol. 25:141], Pichia pastoris [Cregg, et al. (1985) Mol. Cell. Biol. 5:3376; U.S. Pat. Nos. 4,837, 148 and 4,929,555], Saccharomyces cerevisiae [Hinnen et al. (1978) Proc. Natl. Acad. Sci. USA 75:1929; Ito et al.

(1983) *J. Bacteriol.* 153:163], *Schizosaccharomyces pombe* [Beach and Nurse (1981) *Nature* 300:706], and *Yarrowia lipolytica* [Davidow, et al. (1985) *Curr. Genet.* 10:380471 Gaillardin, et al. (1985) *Curr. Genet.* 10:49].

Methods of introducing exogenous DNA into yeast hosts are well-known in the art, and usually include either the transformation of spheroplasts or of intact yeast cells treated with alkali cations. Transformation procedures usually vary with the yeast species to be transformed. See eg., [Kurtz et al. (1986) *Mol. Cell. Biol.* 6:142; Kunze et al. (1985) *J. Basic Microbiol.* 25:141; *Candida*]; [Gleeson et al. (1986) *J. Gen. Microbiol.* 132:3459; Roggenkamp et al. (1986) *Mol. Gen. Genet.* 202:302; *Hansenula*]; [Das et al. (1984) *J. Bacteriol.* 158:1165; De Louvencourt et al. (1983) *J. Bacteriol.* 154:1165; Van den Berg et al. (1990) *Bio/Technology* 8:135; *Kluyveromyces*]; [Cregg et al. (1985) *Mol. Cell. Biol.* 5:3376; Kunze et al. (1985) *J. Basic Microbiol.* 25:141; U.S. Pat. Nos. 4,837,148 and 4,929,555; *Pichia*]; [Hinnen et al. (1978) *Proc. Natl. Acad. Sci. USA* 75;1929; Ito et al. (1983) *J. Bacteriol.* 153:163 *Saccharomyces*]; [Beach and Nurse (1981) *Nature* 300:706; *Schizosaccharomyces*]; [Davidow et al. (1985) *Curr. Genet.* 10:39; Gaillardin et al. (1985) *Curr. Genet.* 10:49; *Yarrowia*].

1. Preparation of LT-A72R Mutant a. Sourc f LT DNA

The 1.5 kb SmaI-EcoRI fragment from plasmid pEWD299, containing the LT-A gene encoding a polypeptide having the sequence of SEQ ID NO:5 and the LTpromoter region [Pronk et al. (1985) J. Biol. Chem. 260:13580; Spicer et al. (1981) Proc. Natl. Acad. Sci. USA 78:50] was subcloned into the Bluescript KS vector (Stratagene). The resultant vector, termed BS-LT-A, was used for site-directed mutagenesis [Zoller & Smith (1982) Nucl. Acid. Res. 10:6487)].

b. Methods of Mutation

Site-directed mutagenesis was performed according to the method of Zoller & Smith [supra] on single-stranded DNA of BS-LT-A vector. The oligonucleotide used:

5'GCTCACTTACGTGGACAGTCT3' (oligoLT-A72R)

mutates the codon for Ala-72 (GCA) to an Arg codon (CGT).

The mutated SmaI-EcoRI fragment containing the mutated codon was ligated with the 0.57 kb EcoRI-HindIII fragment [Pronk et al.; Spicer et al.] containing the gene coding for LT-B and cloned into Bluescript KS vector (Stratagene) to generate vector BS-LTA72R.

c. Expression and Purification of the LT-A72R Mutant.

*E. coli* were transformed with BS-LTA72R vector and grown in LB broth in a 5 liter fermenter. The mutant protein LT-A72R was purified from the periplasm [Pronk et al.; Magagnoli et al. (1996) *Infect Immun* 64:5434] using controlled pore glass (CPG 350, Serva) and A5M Agarose columns and then by gel filtration using Sephacryl S-200™.

An aliquot of the purified material was analysed on a Superdex 200HR column. FIG. 1 shows the elution profile of LT-A72R in comparison with wild-type LT and mutant LTK63 (Ser-63-Lys mutant—see WO93/13202 and also Pizza et al. (1994) *J. Exp. Med.* 6:2147).

LT-A72R elutes as a single peak corresponding to the fully-assembled holotoxin, with a profile identical to that of wild-type LT and LTK63. This demonstrates that the A72R mutation does not alter the structure of the A subunit, that it is efficiently exported to the periplasm, and correctly assembled as $AB_5$. 100 μi aliquots of A72R stored at 4 C were analysed in the same way every two months for a year and no change in elution profile was detected.

2. Physical Characterisation a. Trypsin Digestion

45 μg toxin (LT, LT-A72R, LTK63) was treated with 9 μg trypsin in a final volume of 150 μl 10 mM Tris, pH 7.5, at 37° C. 30 μl samples were collected after 5 and 30 minutes incubation and the reaction was stopped with 3.6 μg trypsin inhibitor. 10 μl 4× concentrated electrophoresis sample buffer was added to each sample and the mixture was heated to 95° C. for 10 minutes. Proteins were loaded onto 15% SDS minigels and either stained with Coomassie brilliant blue R-250 or transferred onto a nitrocellulose membrane, which was subsequently incubated with a rabbit anti-LT polyclonal serum at a dilution of 1:300.

FIG. 2 shows the results of this Western blot analysis. After 5 minutes incubation, trypsin causes almost immediate nicking of the A subunit into A1 and A2 domains, and nicking is complete by 30 minutes. No sensitivity differences were detected between LT, LT-A72R, or LTK63.

b. ADP-Ribosylation of Polyarginine

LT (wild-type and mutant) was analysed as described by Lai et al. [*BBRC* 102:1021, 1981] and the results are shown in FIG. 3.

The ADP-ribosylation activity of LT-A72R is at least 2 orders of magnitude lower than that of wild-type LT: the minimal concentration to obtain a detectable activity was 0.5 μg for LT, and 85 μg for LT-A72R. In contrast, LTK63 is totally devoid of activity.

c. Toxicity

In vitro toxicity was assessed by following the morphological changes caused by LT on Y1 adrenal cells [Donta et al. (1973) *Science* 183:334]. The assay was performed in microtitre plates using 50000 cells/well with twofold dilutions of LT, LT-A72R and LTK63, starting from 80 pg/well for wild-type and 40 μg/well for mutants. Morphological changes were read after 48 hours incubation.

In vivo toxicity was assessed using an ileal loop assay [De (1959) *Nature* 183:1533]. Two New Zealand adult rabbits (ca. 2.5 kg) were used for each assay and 1 ml samples of toxin (wild-type, LT-A72R, LTK63) were injected into each loop at various concentrations, with a control loop receiving 1 ml PBS. After 18–20 hours, the volume of liquid accumulated in each loop was measured with a syringe and the length of each loop was measured again. The results, from 4–6 repeats, expressed as volume of liquid per unit length of the loop (ml/cm) are shown in FIG. 5.

In agreement with the ADP-ribosylation results, LT-A72R had $10^{-5}$ toxicity of wild-type LT on Y1 cells (FIG. 4) and was approximately 20× less toxic than wild-type in the ileal loop assay (FIG. 5). As previously reported, LTK63 was completely non-toxic by both assays.

3. Immunological Characterisation a. Mucosal Adjuvanticity

The adjuvanticity of LT-A72R was tested using the protocol of Douce et al. [*PNAS* 92:1644–1648 (1995)]. Groups of ten BALB/c mice (female, 4–6 weeks old) were immunised intranasally with 1 μg toxin (LT, LT-A72R, LTB, or LK-K63) and 10 μg OVA. The animals were lightly anaes thetised and immunised on day 0, 21 and 35 with a 15 μl volume per nostrel. Immune responses were followed in serum samples taken on days 0, 20, 34 and 52. The animals were sacrificed and nasal lavages were performed by repeated flushing and aspiration of 1 ml PBS containing 0.1% BSA.

LT-specific antibodies were measured using a GM1 capture ELISA. Each well on 96-well plates was first coated with 150 ng GM1 ganglioside by overnight incubation at 4° C. Wells were then washed three times with PBS (+0.05% Tween-20) and 50 ng toxin was added to each well. Plates were incubated at 2 hours at 37° C. OVA-specific antibodies were assessed by coating each well with 60 μg/ml OVA and incubated overnight at 4° C.

The plates were washed and wells saturated with PBS (+1% BSA) for 1 hour at 37° C. Sera from individual mice were tested starting from a dilution of 1:50 in PBS; nasal lavages were tested starting from undiluted. Plates were incubated at 37° C. for 2 hours. Specific Ig were measured using horseradish peroxidase-conjugated rabbit anti-mouse Ig. Antibodies were then revealed by adding o-phenylenediamine as a substrate. After 10 minutes the reaction was blocked by adding 12.5% $H_2SO_4$.

IgG subclasses were determined with IgG1, IgG2a, IgG2b, or IgG3 biotinylated antibodies. Peroxidase-streptavadin was then added to each well (1:1000) and the plates were incubated at 37° C. for 1 hour. Bound antibody was visualised as above.

Absorbances were read at 490 nm and ELISA titres were determined arbitrarily as the reciprocal of the last dilution which gave an $OD_{490} \geq 0.3$ above the level measured in pre-immune sera.

Titres of specific IgA in the sera and in the mucosal lavages were measured using biotin-conjugated goat anti-mouse IgA α chain specific antibody, followed by streptavadin-peroxidase. Bound antibodies were revealed using the OPD substrate as described above. ELISA titres were determined arbitrarily as the reciprocal of the last dilution which gave an $OD_{490} \geq 0.2$ above that of the non-immunised controls.

Values were always normalised using a positive control sample in each plate.

Figure 6:
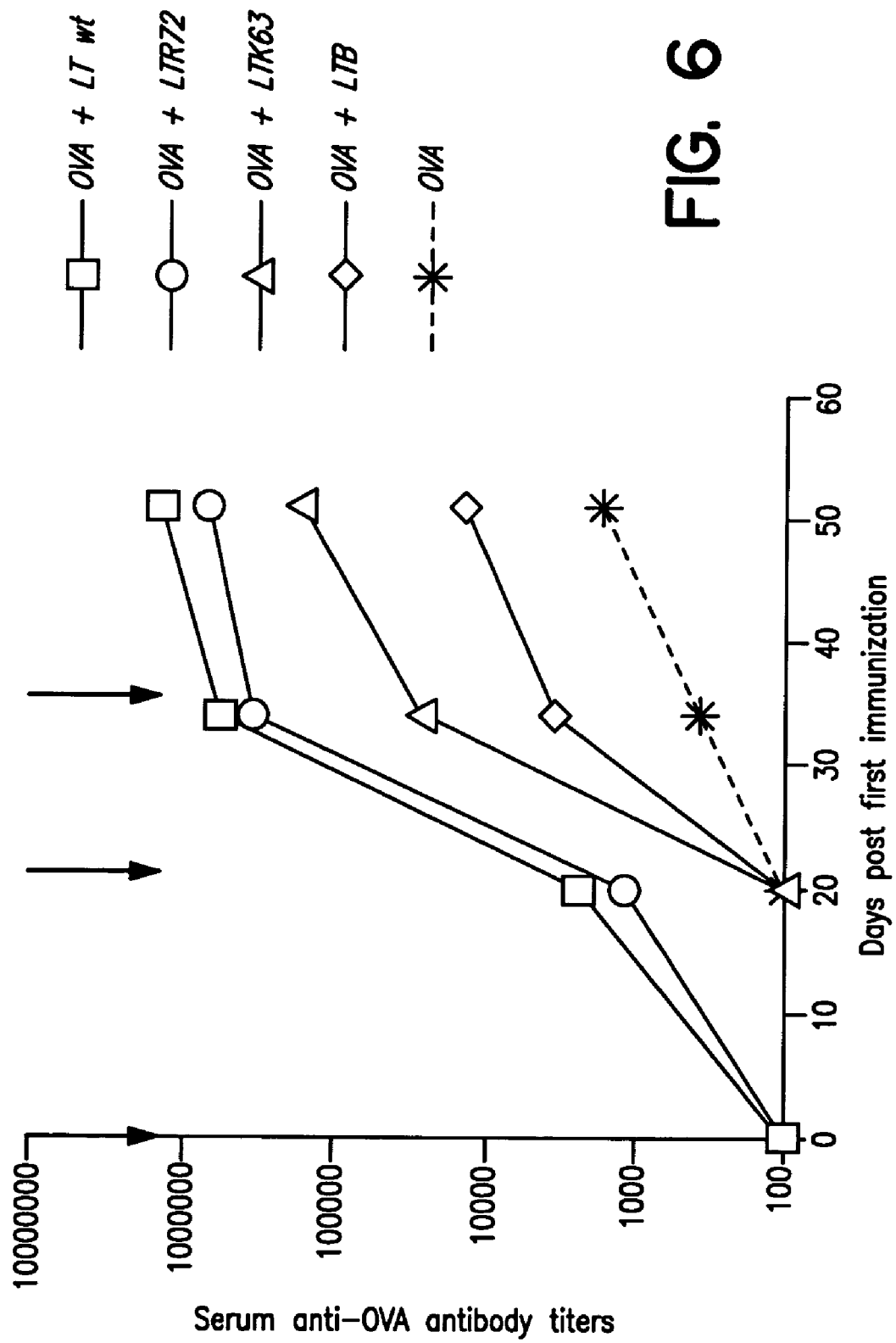
FIG. 6 shows serum anti-OVA antibody response after three intranasal immunisations (indicated by arrows).

As shown in FIG. 6, wild-type LT and LT-A72R induced the highest anti-OVA antibody response. LTK63 induced an intermediate level, and LTB gave a low response. The antigen-specific antibody response was detectable after a single immunisation for wild-type LT and the A72R mutant, whereas (as previously described) LTK63 required at least two immunisations to induce serum anti-OVA antibodies.

Figure 7:
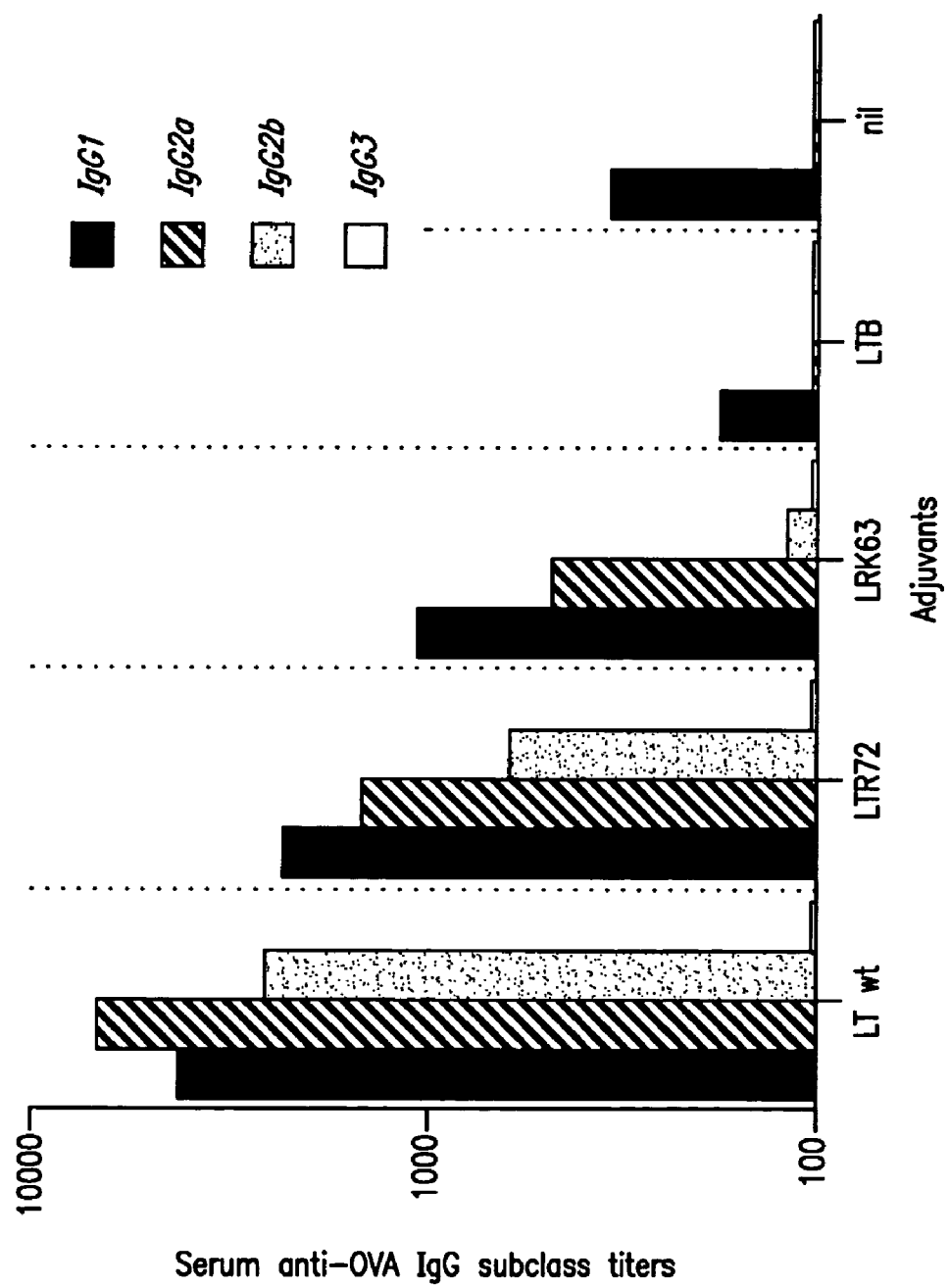
FIG. 7 shows the IgG subclasses after the third immunisation.

OVA-specific IgG isotypes were measured in pools of sera of the last bleeding (FIG. 7). High titres of anti-OVA IgG1, IgG2a and IgG2b were induced in the groups receiving wild-type LT or the A72R mutant as an adjuvant, although the dominant isotype with the mutant was IgG2a. OVA-specific IgG3 antibodies were never detectable. LTB was not a good adjuvant.

Figure 8A:
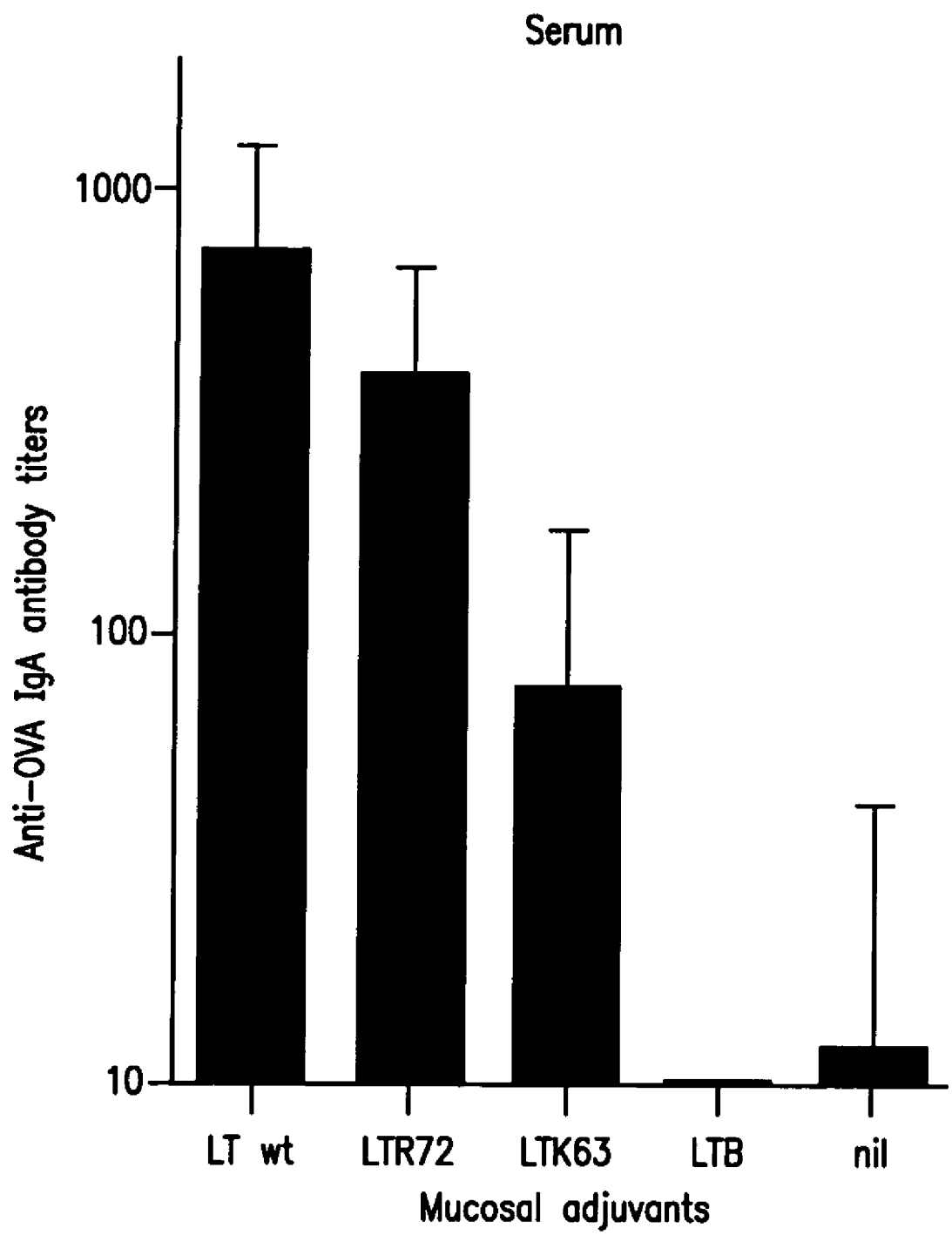
FIG. 8 shows the IgA levels after the third immunisation in serum samples (8A) and nasal washes (8B) [mean titre and standard deviation are shown].
Figure 8B:
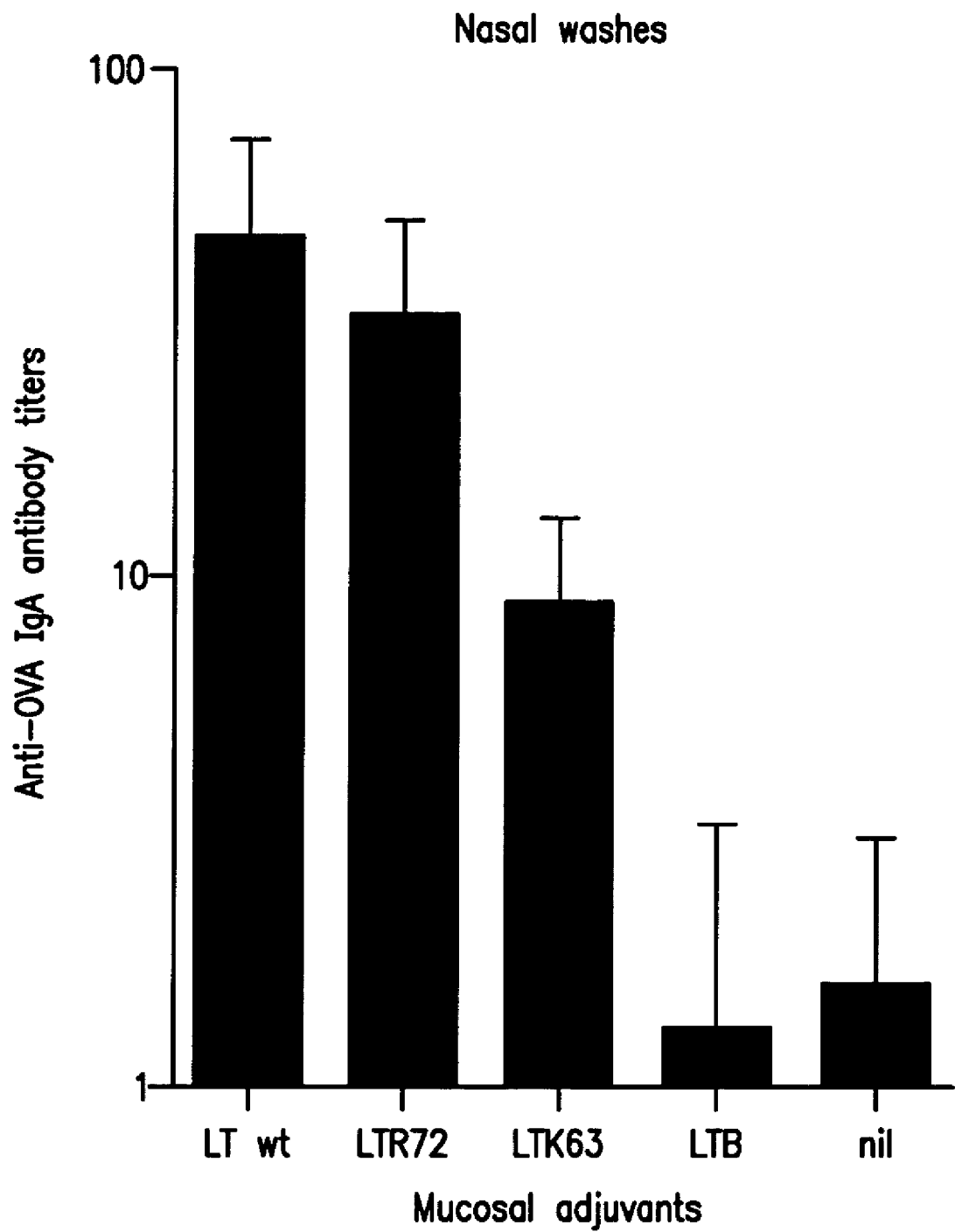

In all experiments, OVA-specific IgA was never detected after just 1 or two intranasal immunisations. Following a third immunisation, however, a serum IgA response was detected with wild-type LT and with the A72R and K63 mutants, but not with LTB (FIG. 8A). A similar pattern was seen at the mucosal level (FIG. 8B), and after three immunisations OVA-specific IgA was found in the nasal washes of the wild-type group and the A72R and K63 mutant groups, but not in the control or LTB groups.

Figure 9A:
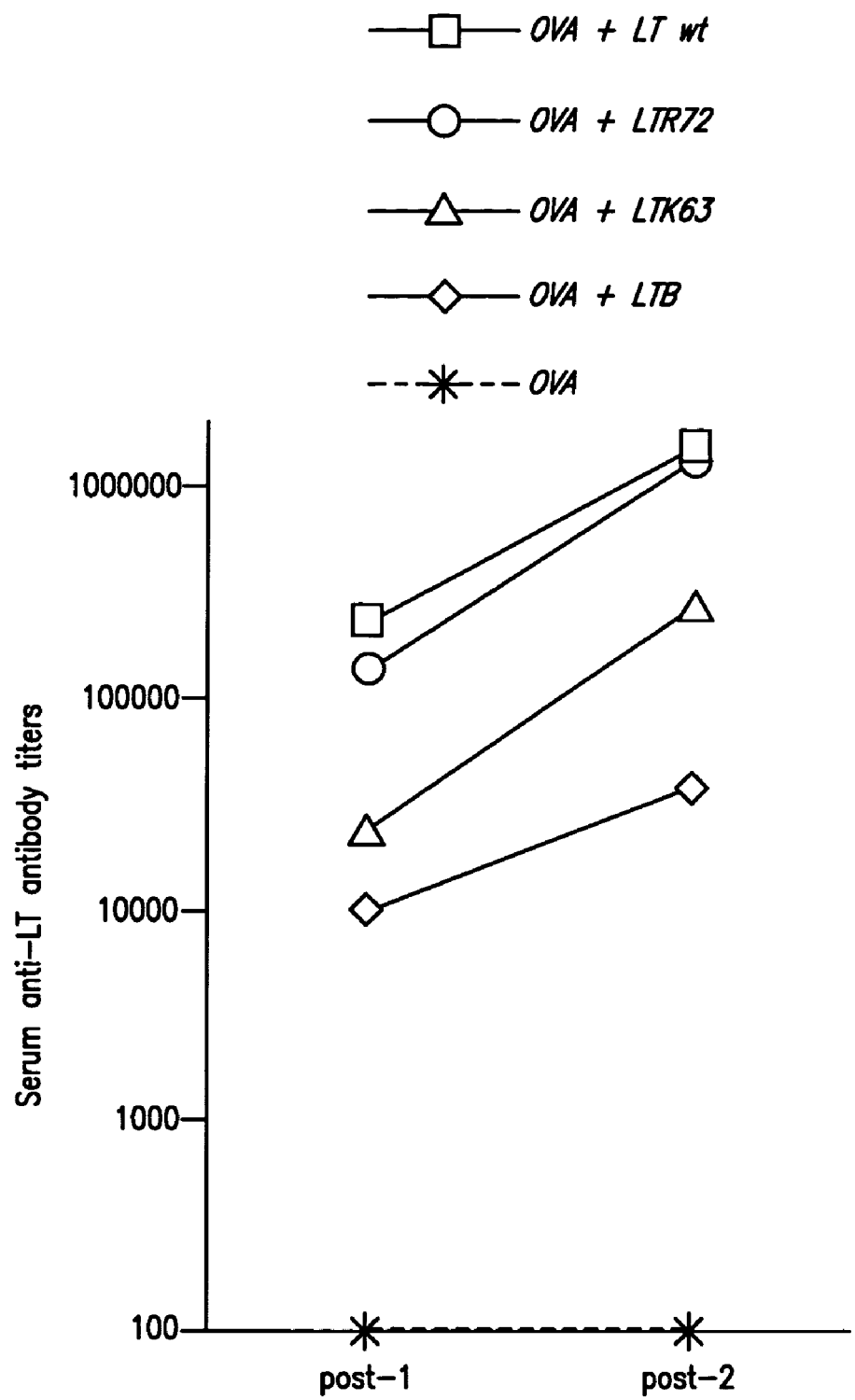
FIG. 9 shows serum anti-LT Ig (9A) and IgA (9B) responses.
Figure 9B:
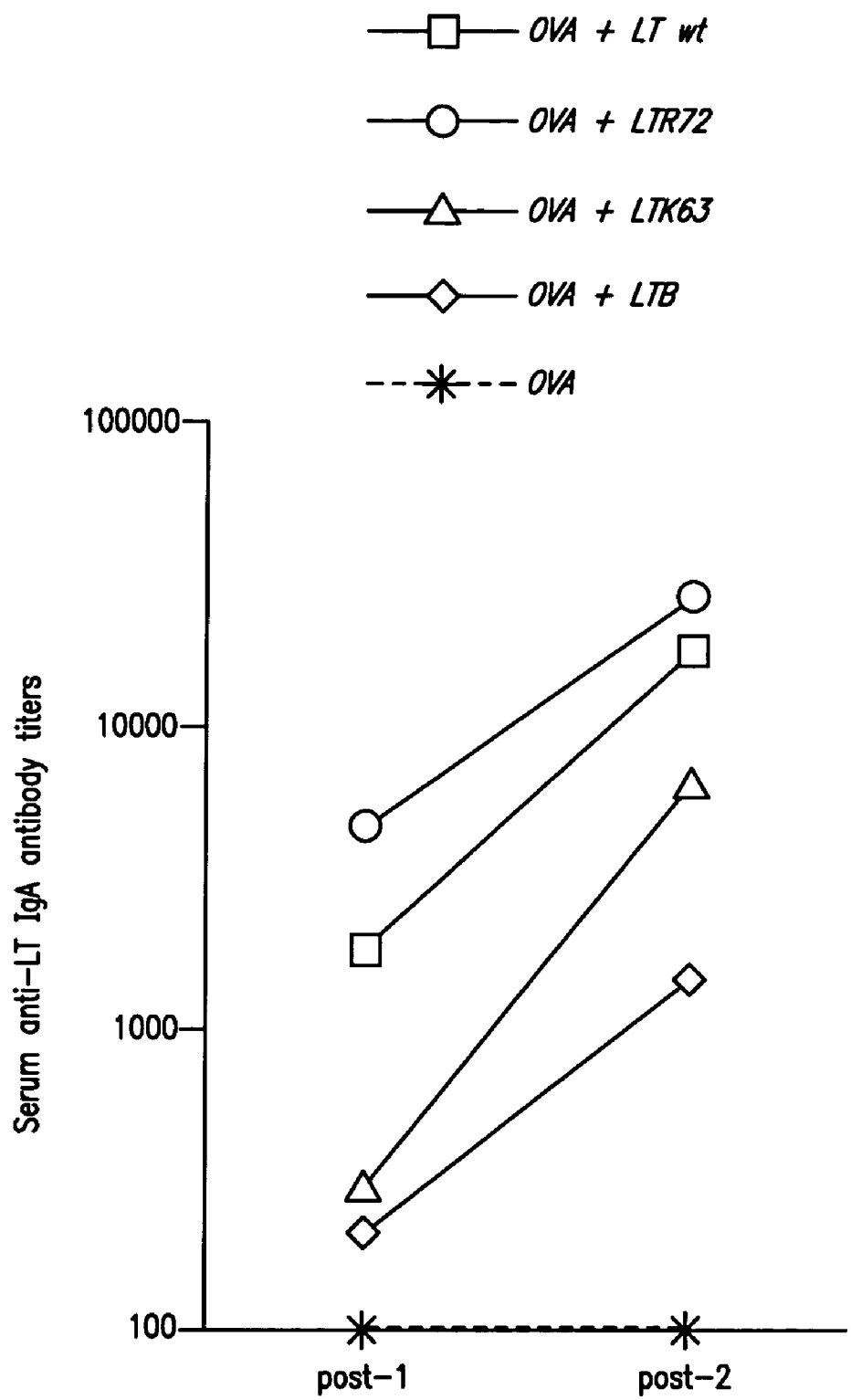

Serum anti-LT antibody responses are shown in FIG. 9. The mice mounted responses after the first immunisation, which was significantly boosted by the second. The A72R mutant was more immunogenic that the non-toxic K63 mutant, and both were much more immunogenic than LTB.

b. OVA-Driven Proliferative Response

Figure 10:
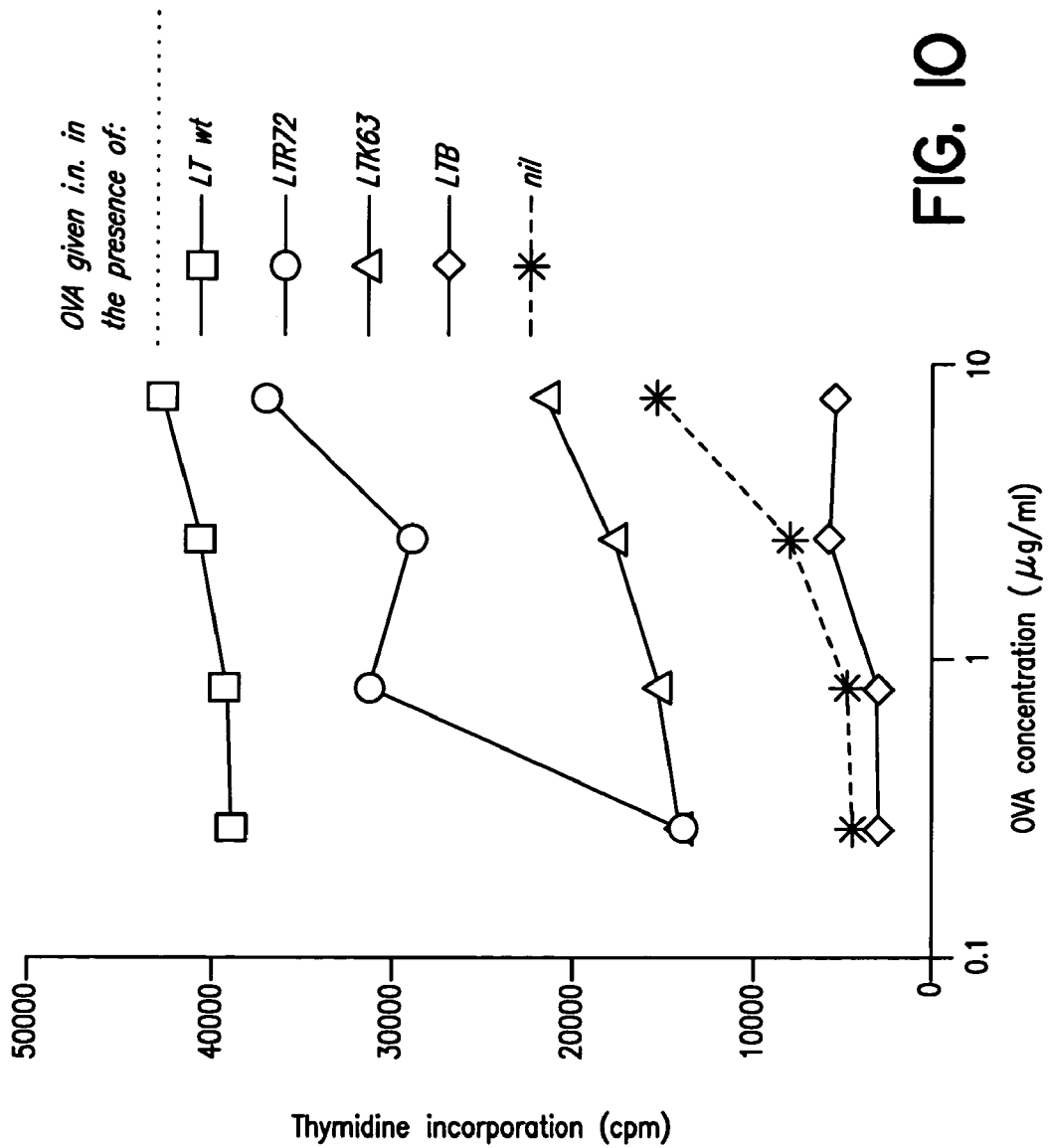
FIG. 10 shows OVA-driven proliferative responses. Background values (no OVA added to clutures) varied between 1000 and 3000 cpm.

14–20 days after 2 or 3 intranasal immunisations with OVA+LT (wild-type or mutant), 2 or 3 mice per group were sacrificed and spleens removed. Spleen cell suspensions were obtained and resuspended in complete DMEM (10% FCS, 2 mM L-glutamine, 15 mM Hepes, 100 U penicillin/streptomycin, 50 mM 2-mercapto-ethanol). $2 \times 10^5$ spleen cells/well were seeded in U-bottomed 96-well plates and cultured in the presence of different concentrations of OVA for 5 days. [$^3$H]-thymidine was added (1 μCi/well) 16 hours before the end of culture. Cells were then harvested with a cell harvester, and [$^3$H]-thymidine incorporation was evaluated by liquid scintillation counting (FIG. 10).

It is clear that intranasal co-administration of antigen with wild-type or with A72R or K63 mutants induced a priming of OVA-specific T cells in vivo, which was much stronger than that detectable after immunisation with OVA alone or with OVA+LTB.

c. In Vivo Challenge

The $LD_{50}$ for LT was determined by inoculating groups of 10 BALB/c mice (female, 9 weeks old) intraperitoneally with LT (12.5 μg, 25 μg, 50 μg, or 100 μg) or PBS. After 7 days of observation, $LD_{50}$ was determined as 20.4 μg.

Four week old BALB/c mice were immunised intranasally at day 0 and 21 with 1 μg toxin (LT, LT-A72R, LT-K63, or LTB) and challenged with LT ($2 \times LD_{50}$) at day 35. They were observed for death for 7 days. Sera were collected at days 0, 20 and 35 and anti-LT titres analysed by ELISA (as above).

Figure 11A:
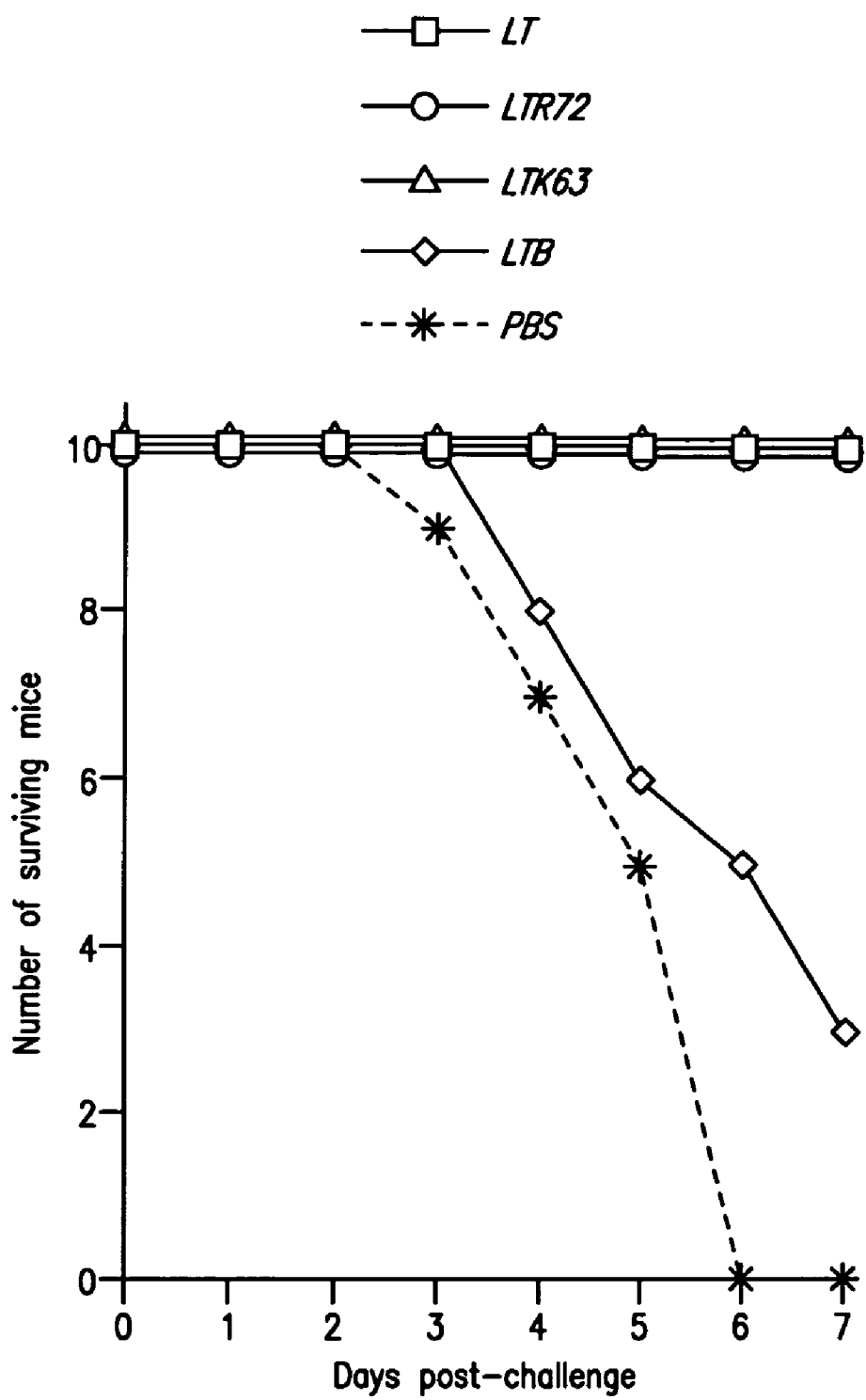
FIG. 11 shows the efficacy against systemic challenge of intranasal immunisation with wild-type LT and with mutants A72R and K63. Columns in 11B are mean titres and dots are individual titres. Black dots show titres from mice immunised with LTB and not protected against challenge.

All mice immunised with wild-type or mutant LT survived to the challenge, whereas only 30% of those receiving LTB survived. All mice in the control group died (FIG. 11A).

Figure 11B:
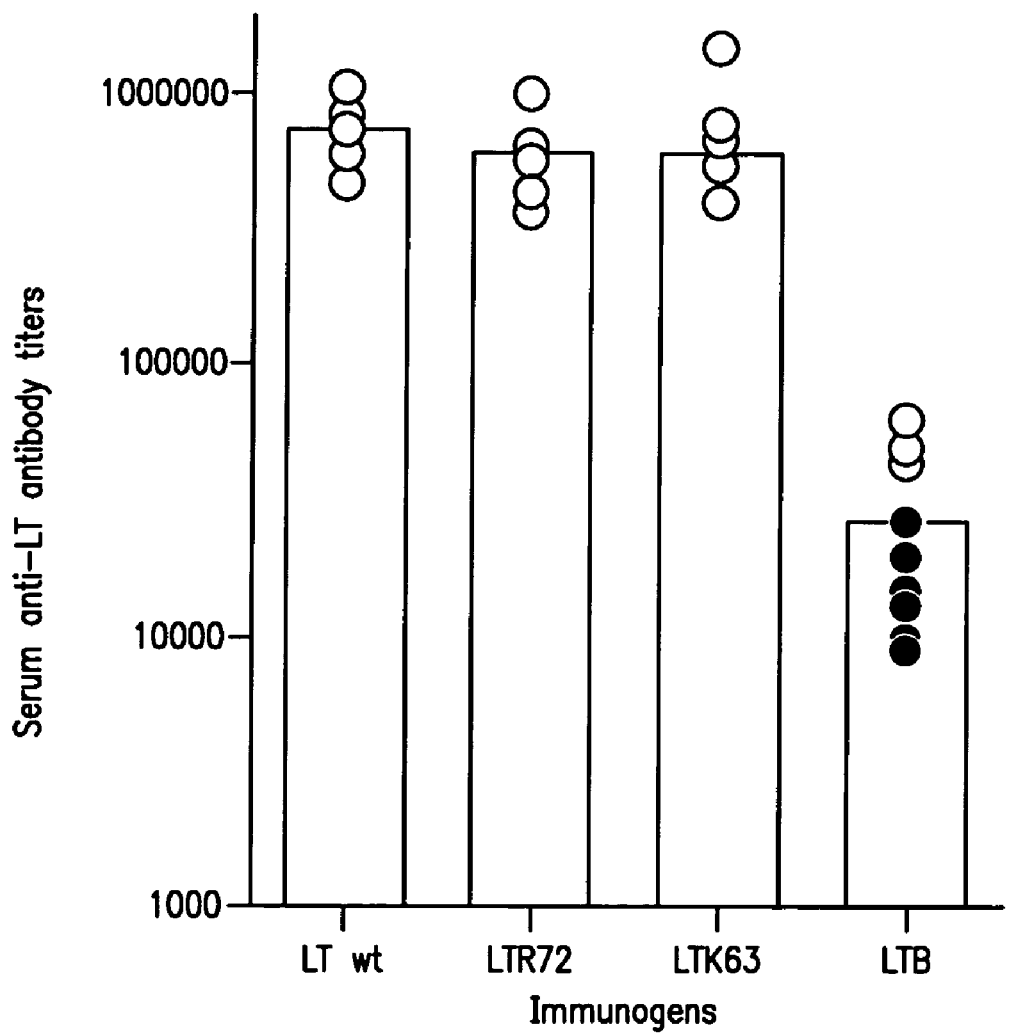

Sera of mice immunised with wild-type LT, or with the A72R or K63 mutants, contained very high and comparable levels of anti-LT antibodies (FIG. 11B). In mice receiving LTB, however, the titres were 10–20× lower. The three LTB mice who survived to the LT challenge (open circles) had significantly higher titres than those in the dead animals.

4. Conclusions

ADP-ribosylation activity is not necessary for the adjuvanticity of LT, but the presence of low levels of enzymatic activity may be useful to induce a faster and higher immune response to co-administered antigens.

The A72R mutant of LT is an effective mucosal adjuvant. In addition, the mutant retains the immunogenicity of wild-type LT and is able to induce protective immunity against LT. It may therefore also be useful for anti-diarrhoea vaccination.

It will, of course, be understood that the invention is described above by way of example only and modifications may be made within the scope and spirit of the invention.

The invention claimed is:

1. A polynucleotide encoding an immunologically effective detoxified *E. coli* heat labile toxin (LT-A) polypeptide, wherein the polypeptide comprises SEQ ID NO:1, and further wherein the amino acid residue corresponding to Ala